(12) United States Patent
Kothandaraman et al.

(10) Patent No.: US 10,961,173 B2
(45) Date of Patent: Mar. 30, 2021

(54) INTEGRATED CAPTURE AND CONVERSION OF $CO_2$ TO METHANOL OR METHANOL AND GLYCOL

(71) Applicant: Battelle Memorial Institute, Richland, WA (US)

(72) Inventors: Jotheeswari Kothandaraman, Richland, WA (US); David J. Heldebrant, Richland, WA (US); Yuan Jiang, Richland, WA (US); Robert A. Dagle, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 16/928,649

(22) Filed: Jul. 14, 2020

(65) Prior Publication Data

US 2021/0017108 A1    Jan. 21, 2021

Related U.S. Application Data

(60) Provisional application No. 63/038,464, filed on Jun. 12, 2020, provisional application No. 62/874,383, filed on Jul. 15, 2019.

(51) Int. Cl.
*C07C 29/132* (2006.01)
*B01J 31/18* (2006.01)
*B01J 31/24* (2006.01)
*B01J 31/20* (2006.01)

(52) U.S. Cl.
CPC .......... *C07C 29/132* (2013.01); *B01J 31/189* (2013.01); *B01J 31/20* (2013.01); *B01J 31/2409* (2013.01); *B01J 2231/646* (2013.01); *B01J 2531/821* (2013.01)

(58) Field of Classification Search
CPC ....... C07C 29/132; B01J 31/189; B01J 31/20; B01J 31/2409; B01J 2231/646; B01J 531/821
USPC .......................................................... 568/864
See application file for complete search history.

(56) References Cited

FOREIGN PATENT DOCUMENTS

| CN | 104807864 B | 7/2018 |
|---|---|---|
| WO | WO 2018-162611 A1 | 9/2018 |

OTHER PUBLICATIONS

Baccar, H. et al., "Interdigitated Microelectrode Array Integrated in Microfluidic Cell for Biosensor Applications," *Journal of Nanomedicine & Nanotechnology*, 2014, vol. 5, No. 6, pp. 1-4.

Barpaga, D. et al., "Probing the Sorption of Perfluorooctanesulfonate Using Mesoporous Metal-Organic Frameworks from Aqueous Solutions," *Inorganic Chemistry*, May 8, 2019, vol. 58, No. 13, pp. 8339-8346, pp. 8339-8342.

(Continued)

*Primary Examiner* — Deborah D Carr
(74) *Attorney, Agent, or Firm* — Klarquist Sparkman, LLP

(57) ABSTRACT

A process for producing methanol includes combining a hydrogenation catalyst, hydrogen, and $CO_2$ with a condensed phase solution comprising an amine under conditions effective to form methanol and water. A process for coproduction of methanol and a glycol includes combining an epoxide, a hydrogenation catalyst, hydrogen, and $CO_2$ with a condensed phase solution comprising an amine under conditions effective to form methanol and a glycol.

20 Claims, 16 Drawing Sheets

(56) References Cited

OTHER PUBLICATIONS

International Search Report and Written Opinion, dated Aug. 20, 2020, issued in International Application No. PCT/US2020/031940, 9 pages.

Liu, X.-W. et al., "Composites of metal-organic frameworks and carbon-based materials: Preparations, functionalities and applications," *Journal of Materials Chemistry A*, 2016, vol. 4, No. 10, pp. 3584-361.

Bobbink et al., "Synthesis of Methanol and Diols from $CO_2$ via Cyclic Carbonates under Metal-Free, Ambient Pressure, and Solvent-Free Conditions," *ACS Sustainable Chem. Eng.* 2018, 6:12119-12123.

Heldebrant et al, "Performance of single-component $CO_2$-binding organic liquids ($CO_2BOLs$) for post combustion $CO_2$ capture," Chem. Eng. J. (2011), doi:10.1016/j.cej.2011.02.012 (7 pages).

Katihal et al., "Catalytic Hydrogenation of Cyclic Carbonates using Manganese Complexes," *Angew. Chem.* 2018, 130:13637-13641.

Lao et al, "The steps of activating a prospective $CO_2$ hydrogenation catalyst with combined $CO_2$ capture and reduction," *Green Chem.* 2016, 18:4871-4874.

Pérez-Fortes et al., "Methanol synthesis using captured $CO_2$ as raw material: Techno-economic and environmental assessment," *Applied Energy* 2016, published online Aug. 12, 2015, 161:718-732.

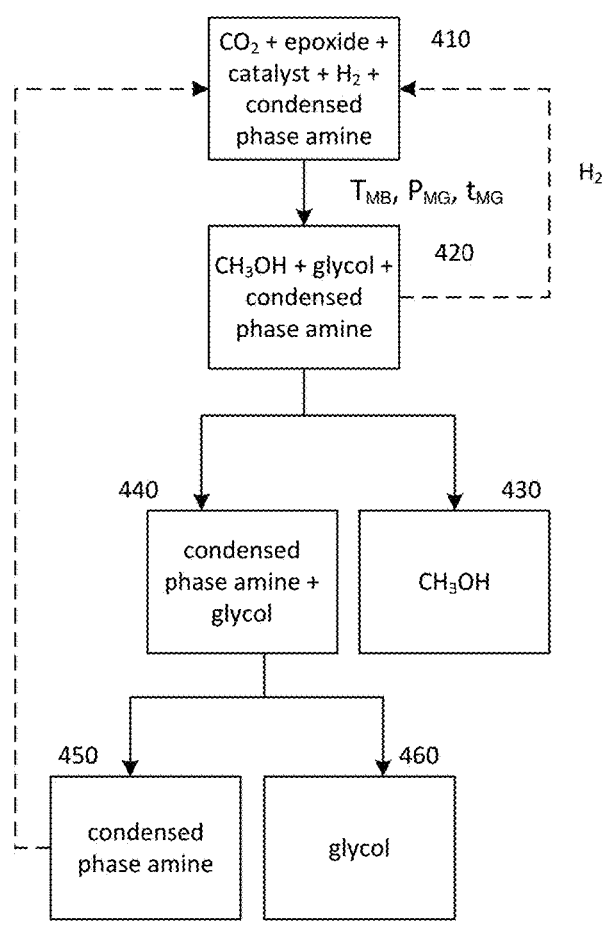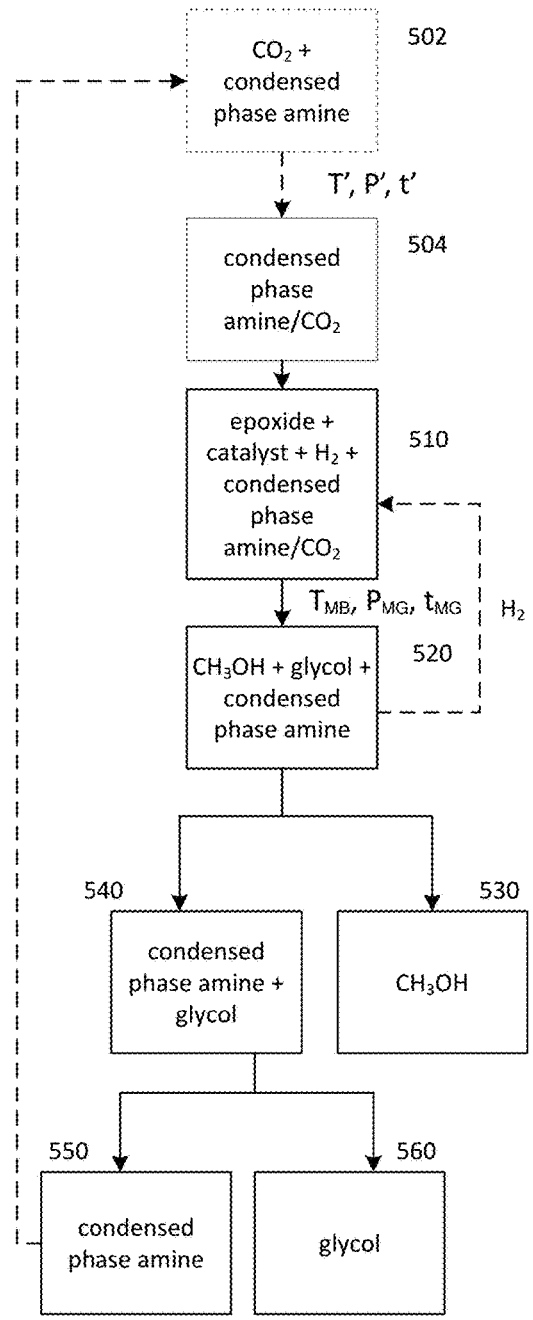
FIG. 4
FIG. 5

INTEGRATED CAPTURE AND CONVERSION OF $CO_2$ TO METHANOL OR METHANOL AND GLYCOL

CROSS-REFERENCE TO RELATED APPLICATIONS

This application claims the benefit of the earlier filing date of U.S. Provisional Application No. 63/038,464, filed Jun. 12, 2020, and U.S. Provisional Application No. 62/874,383, filed Jul. 15, 2019, each of which is incorporated by reference herein in its entirety.

ACKNOWLEDGMENT OF GOVERNMENT SUPPORT

This invention was made with Government support under Contract DE-AC05-76RL01830 awarded by the U.S. Department of Energy. The Government has certain rights in the invention.

FIELD

This invention is directed to an integrated process for capture and conversion of $CO_2$ to methanol or a combination of methanol and glycol.

SUMMARY

This disclosure concerns embodiments of an integrated process for capture and conversion of $CO_2$ to methanol or concurrently to methanol and a glycol. In some embodiments, the process is a one-step process. In other embodiments, the process is a two-step process. The process may be a one-pot process. In some embodiments, the process is continuous.

In some embodiments, an integrated process includes producing methanol by combining a hydrogenation catalyst, hydrogen, and $CO_2$ with a condensed phase comprising an amine under conditions effective to provide a reaction between the hydrogen and $CO_2$ to form methanol and water. The methanol and water are separated. In certain embodiments, the conditions effective to form methanol and water include (i) a temperature $T_M$ within a range of from 50-180° C., or (ii) an initial pressure $P_M$ within a range of from 1 MPa to 10 MPa, or (iii) a time $t_M$ within a range of from 3 seconds to 36 hours, or (iv) any combination of (i), (ii), and (iii).

In some embodiments, an integrated process includes producing methanol and a glycol by combining an epoxide, a hydrogenation catalyst, hydrogen, and $CO_2$ with a condensed phase comprising an amine under conditions effective to provide a reaction between the epoxide, hydrogen, and $CO_2$ to form methanol and the glycol. In some embodiments, the conditions effective to form methanol and the glycol include (i) a temperature $T_{MG}$ within a range of from 50° C. to 170° C., or (ii) an initial pressure $P_{MG}$ within a range of from 3 MPa to 10 MPa, or (iii) a time $t_{MG}$ within a range of from 3 seconds to 36 hours, or (iv) any combination of (i), (ii), and (iii).

The epoxide comprises

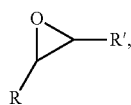

and the glycol comprises R—CH(OH)—CH(R') (OH), where R and R' independently are H or aliphatic, or R and R' together with the carbon atoms to which they are attached form a cycloaliphatic ring. In some embodiments, R is methyl and R' is H.

In any of the foregoing or following embodiments, the process may further include combining the epoxide, the $CO_2$, and the condensed phase under cycloaddition conditions effective to form a cyclic carbonate, thereby producing a cyclic carbonate-containing mixture, and subsequently combining the cyclic carbonate-containing mixture with the hydrogenation catalyst and hydrogen under conditions effective to concurrently form methanol and the glycol. Alternatively, in any of the foregoing or following embodiments, the process may further include forming a mixture by combining the epoxide, the hydrogen catalyst, and the $CO_2$ with the condensed phase, exposing the mixture to cycloaddition conditions effective to form a cyclic carbonate, thereby producing a cyclic carbonate-containing mixture, and combining the cyclic carbonate-containing mixture with hydrogen under conditions effective to form methanol and the glycol. In some embodiments, the cycloaddition conditions effective to form a cyclic carbonate comprise (i) a temperature $T_C$ within a range of from 25° C. to 180° C., or (ii) an initial pressure $P_C$ within a range of from 0.1 MPa to 2 MPa, or (iii) a time $t_C$ within a range of from 3 seconds to 36 hours, or (iv) any combination of (i), (ii), and (iii).

In any of the foregoing or following embodiments, the amine may comprise a 1° amine group, a 2° amine group, a 3° amine group, or any combination thereof. In any of the foregoing or following embodiments, the $CO_2$ may be adsorbed, absorbed, covalently, or ionically bound to the amine. In some embodiments, the amine comprises a polyamine, a tertiary amine, a compound according to Formula I, or any combination thereof, the compound according to Formula I having a structure $R^1(R^2)N-L^1-NH-R^3$ where each of $R^1$ and $R^2$ independently is aliphatic or cycloaliphatic or $R^1$ and $R^2$ together with the nitrogen to which they are attached form a heterocyclyl ring, $L^1$ is aliphatic or cycloaliphatic or $L^1$ and $R^1$ together with the nitrogen to which they are attached form a heterocyclyl ring, and $R^3$ is aliphatic, cycloaliphatic, cycloalkylalkyl or alkoxyalkyl.

In any of the foregoing embodiments, the condensed phase may be a condensed phase comprising the $CO_2$ prior to combination with the other components. In such embodiments, the condensed phase may be prepared by contacting a gas stream comprising $CO_2$ with an amine-containing solvent or solution prior to combing the condensed phase solution with the remaining components. In some embodiments, contacting the gas stream with the amine-containing solvent or solution is performed (i) at a temperature T' within a range of from 20° C. to 60° C., or (ii) at an initial pressure P' within a range of from 0.1 MPa to 5 MPa, or (iii) both (i) and (ii).

In any of the foregoing or following embodiments, the hydrogenation catalyst may comprise known materials to catalyze hydrogenation such as (i) precious metals Pt, Pd, Rh, Ir, and Ru, base metals Ni, Co, Fe, Cu, and Zn, and catalysts supported on materials such as alumina, silica, carbon, and chromite and magnesium aluminum spinels, or any combination thereof; or (ii) a pincer ligand; or (iii) both (i) and (ii).

BRIEF DESCRIPTION OF THE FIGURES

FIG. 4 is a flow diagram of one exemplary embodiment of a process for converting CO$_2$ to methanol and a glycol.

FIG. 5 is a flow diagram of another exemplary embodiment of a process for converting CO$_2$ to methanol and a glycol.

DETAILED DESCRIPTION

Figures 1, 2:
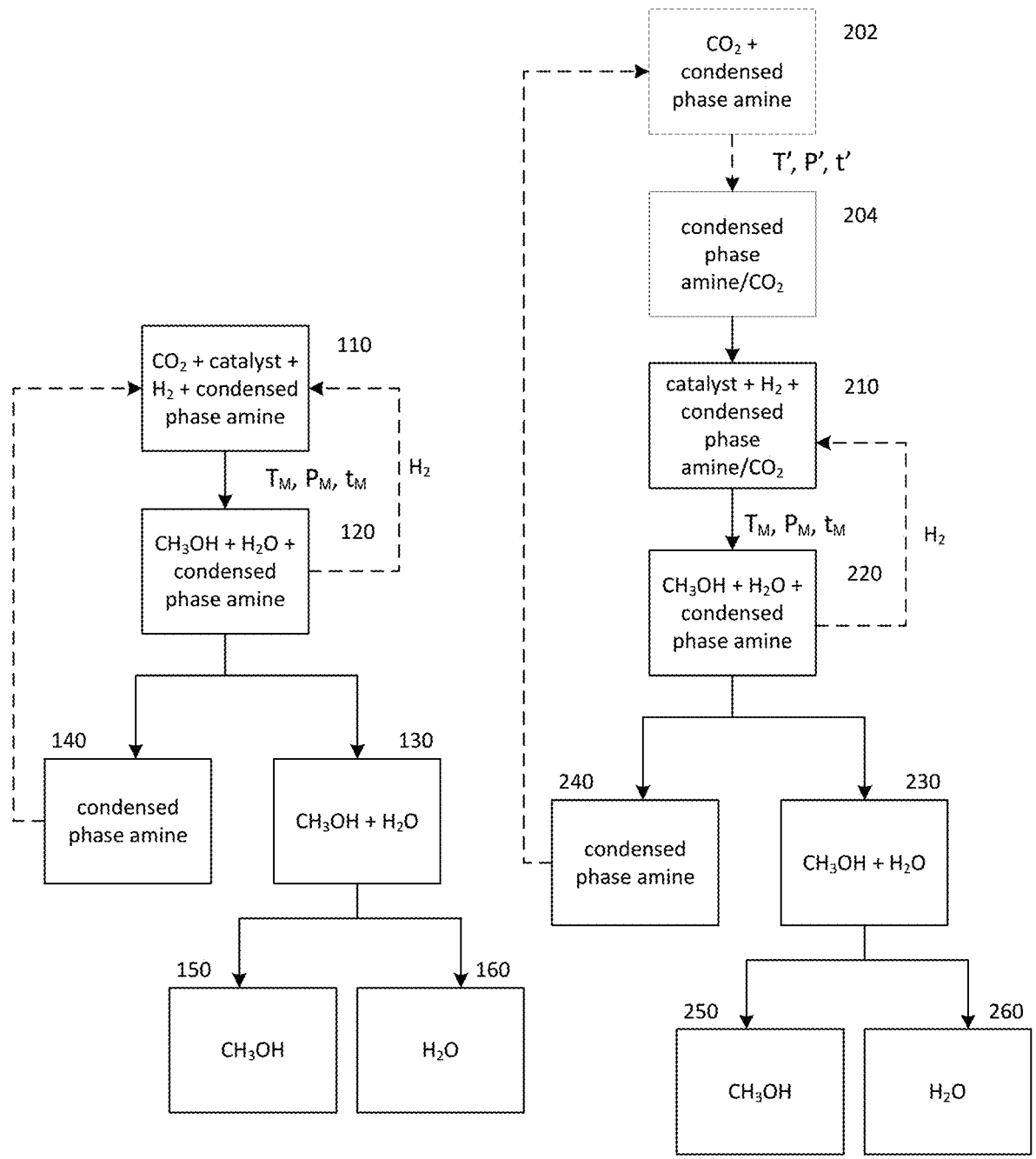
FIG. 1 is a flow diagram of one exemplary embodiment of a process for converting $CO_2$ to methanol.
FIG. 2 is a flow diagram of another exemplary embodiment of a process for converting CO$_2$ to methanol.

Embodiments of an integrated process for capture and conversion of CO$_2$ to methanol or to methanol and a glycol are disclosed. Methanol is a commodity chemical that can be used as a feedstock to produce olefins, ethers, fuel blends, acetic acid, and other products. Glycols, such as ethylene glycol and propylene glycol, are used as automotive antifreeze, chemical feedstocks for polyester production, and for other miscellaneous applications.

Industrially, methanol typically is produced from a syngas mixture in the presence of a Cu-based catalyst at high temperature and high pressure as shown below. The reaction byproduct, water, is separated from methanol by distillation and is not utilized in the process, which lowers the net theoretical atom efficiency to ~73%.

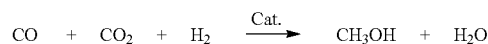

Glycols are typically produced by hydrolysis of epoxide in excess water under acidic conditions at high temperature (>150° C.). In addition, the hydrolysis product stream is often contaminated with oligomers of glycols because the product glycol reacts faster with epoxide than water. The use of excess water (~20-fold molar excess) is necessary to reduce the formation of higher homologues, and there is an energy penalty associated with separation of glycol(s) from excess water and oligomers.

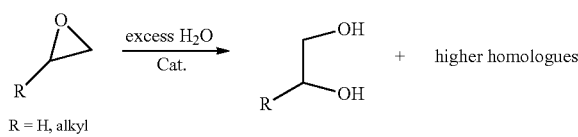

In the case of ethylene oxide-to-ethylene glycol conversion, a two-step Shell OMEGA process (shown below) involving the formation of a cyclic carbonate and subsequent hydrolysis of the cyclic carbonate to ethylene glycol is practiced industrially to improve the selectivity for the glycol. However, the process still involves an energy-intensive separation process to remove excess water from the product.

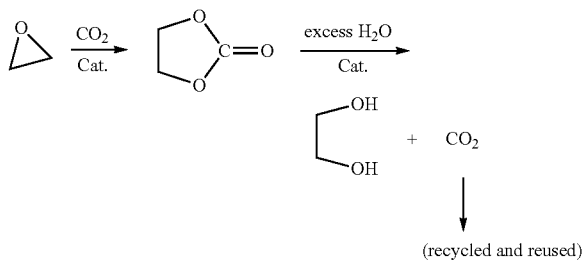

Another known two-step process reacts CO$_2$ with an epoxide (R is H or alkyl) to form a cyclic carbonate, which is reduced with a hydrosilane and N-tetrabutylammonium fluoride (TBAF) to form a glycol and methanol (Bobbink et al., ACS Sustainable Chem. Eng. 2018, 6:12119-12123). A major disadvantage is the silane waste produced.

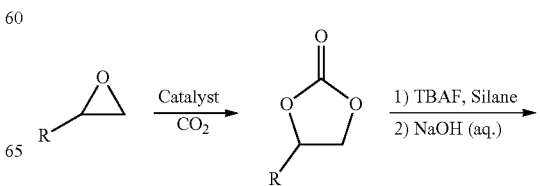

-continued

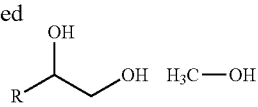

Embodiments of the foregoing processes suffer from additional disadvantages including a requirement for added water and, in some cases, an added base. The foregoing processes also may require base-assisted aqueous work-up, thereby complicating the separation process.

Embodiments of the disclosed integrated process provide advantages over the foregoing processes. In some embodiments, the integrated process reduces energy requirements, simplifies equipment, eliminates one or more separations of excess reagents and/or byproducts, reduces waste, and/or improves atom efficiency. Embodiments of the discloses integrated process do not require added water and/or form products that can be simply separated, e.g., by distillation. Instead, in some embodiments, reactant water is formed and consumed in situ.

In some embodiments, an integrated process for producing methanol includes combining a hydrogenation catalyst, hydrogen, and $CO_2$ with a condensed phase comprising an amine under conditions effective to form methanol and water. In some embodiments, an integrated process for coproducing methanol and a glycol includes combining an epoxide, a hydrogenation catalyst, hydrogen, and $CO_2$ with a condensed phase comprising an amine under conditions effective to form methanol and a glycol.

In some embodiments, the integrated process is a one-step process. In other embodiments, the process is a two-step process. The process may be continuous. The $CO_2$ and $H_2$ utilized in embodiments of the disclosed processes may be obtained from any suitable source. In some embodiments, the $CO_2$ is obtained from landfill gases, wastewater treatment gases, manure gas sources, or other industrial processes. $CO_2$ is captured using a condensed phase amine. In contrast to existing technologies, subsequent conversion to methanol or methanol and glycol is performed in the condensed phase amine. Advantageously, embodiments of the disclosed processes eliminate the need to separate and compress $CO_2$ for gas-phase hydrogenation and the accompanying energy requirement for the separation and compression. In some embodiments, hydrogenation is performed in the condensed phase at a lower temperature than those required for gas phase hydrogenation. These advantages render embodiments of the disclosed integrated capture and conversion process more economically viable than existing technologies.

I. Definitions

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

The disclosure of numerical ranges should be understood as referring to each discrete point within the range, inclusive of endpoints, unless otherwise noted. Unless otherwise indicated, all numbers expressing quantities of components, molecular weights, percentages, temperatures, times, and so forth, as used in the specification or claims are to be understood as being modified by the term "about." Accordingly, unless otherwise implicitly or explicitly indicated, or unless the context is properly understood by a person of ordinary skill in the art to have a more definitive construction, the numerical parameters set forth are approximations that may depend on the desired properties sought and/or limits of detection under standard test conditions/methods as known to those of ordinary skill in the art. When directly and explicitly distinguishing embodiments from discussed prior art, the embodiment numbers are not approximates unless the word "about" is recited.

Although there are alternatives for various components, parameters, operating conditions, etc. set forth herein, that does not mean that those alternatives are necessarily equivalent and/or perform equally well. Nor does it mean that the alternatives are listed in a preferred order unless stated otherwise.

Definitions of common terms in chemistry may be found in Richard J. Lewis, Sr. (ed.), *Hawley's Condensed Chemical Dictionary*, published by John Wiley & Sons, Inc., 2016 (ISBN 978-1-118-13515-0).

Aliphatic: A substantially hydrocarbon-based compound, or a radical thereof (e.g., $C_6H_{13}$, for a hexane radical), including alkanes, alkenes, alkynes, including cyclic versions thereof (cycloaliphatic), and further including straight- and branched-chain arrangements, and all stereo and position isomers as well. Unless expressly stated otherwise, an aliphatic group contains from one to twenty-five carbon atoms; for example, from one to fifteen, from one to ten, from one to six, or from one to four carbon atoms. The term "lower aliphatic" refers to an aliphatic group containing from one to ten carbon atoms. An aliphatic chain may be substituted or unsubstituted. Unless expressly referred to as an "unsubstituted aliphatic," an aliphatic group can either be unsubstituted or substituted.

Alkoxyalkyl: A radical having the general formula —R—O—R' where R and R' independently are alkyl.

Amine: A compound including an amino group —N(R)R' where R and R' are independently hydrogen, alkyl, heteroalkyl, haloalkyl, aliphatic, heteroaliphatic, aryl (such as optionally substituted phenyl or benzyl), heteroaryl, alkylsulfano, or other functionality. A 1°, or primary, amine includes an —$NH_2$ group. A 2°, or secondary, amine includes an —N(H)R group. A 3°, or tertiary, amine includes an —N(R)R' group. A polyamine is an organic compound having more than two amino groups.

Aromatic or aryl: A monovalent aromatic carbocyclic group of, unless specified otherwise, from 6 to 15 carbon atoms having a single ring (e.g., phenyl) or multiple condensed rings in which at least one ring is aromatic (e.g., quinoline, indole, benzodioxole, and the like), provided that the point of attachment is through an atom of an aromatic portion of the aryl group and the aromatic portion at the point of attachment contains only carbons in the aromatic ring. If any aromatic ring portion contains a heteroatom, the group is a heteroaryl and not an aryl. Aryl groups are monocyclic, bicyclic, tricyclic or tetracyclic.

Catalyst: A substance, usually present in small amounts relative to reactants, which increases the rate of a chemical reaction without itself being consumed or undergoing a chemical change. A catalyst also may enable a reaction to proceed under different conditions (e.g., at a lower temperature) than otherwise possible.

Condensed phase: The term "condensed phase" refers to a liquid or solid phase, including liquid/liquid, liquid/solid, and solid/solid solutions and mixtures.

Cyclic carbonate: A compound having a general formula

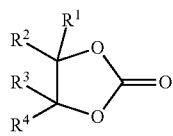

where $R^1$-$R^4$ independently are H or aliphatic. In some disclosed embodiments, $R^1$ is aliphatic, such as $C_1$-$C_5$ alkyl, and $R^2$-$R^4$ are H.

Cycloaddition: As used herein, cycloaddition refers to addition of $CO_2$ to an epoxide, resulting in a cyclic carbonate.

Cycloalkylalkyl: A radical having a general formula —R—R' where R is alkyl and R' is cycloalkyl, e.g., —CH$_2$-cycloalkyl.

Epoxide: A cyclic ether with a 3-membered ring having a general formula

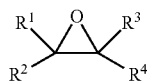

where $R^1$-$R^4$ independently are H or aliphatic, e.g., $C_1$-$C_5$ alkyl. In some cases, $R^2$ and $R^4$ together with the carbon atoms to which they are attached form a cycloaliphatic ring.

Glycol: A dihydric alcohol (a diol) in which the two hydroxyl groups are on different carbon atoms, typically two adjacent carbon atoms.

Heteroaliphatic: An aliphatic compound or group having at least one carbon atom in the chain and at least one heteroatom, i.e., one or more carbon atoms has been replaced with an atom having at least one lone pair of electrons, typically nitrogen, oxygen, phosphorus, silicon, or sulfur. Heteroaliphatic compounds or groups may be substituted or unsubstituted, branched or unbranched, cyclic or acyclic, and include "heterocycle", "heterocyclyl", "heterocycloaliphatic", or "heterocyclic" groups.

Heteroaryl: An aromatic compound or group having at least one heteroatom, i.e., one or more carbon atoms in the ring has been replaced with an atom having at least one lone pair of electrons, typically nitrogen, oxygen, phosphorus, silicon, or sulfur.

Heterocyclyl ring: Refers to a closed-ring compound, or radical thereof as a substituent bonded to another group, particularly other organic groups, where at least one atom in the ring structure is other than carbon, and typically is oxygen, sulfur and/or nitrogen. Pincer ligand: A tridentate chelating ligand that forms three bonds to a metal cation to form a complex. Typically, a pincer ligand binds to three adjacent coplanar sites on the metal cation in a meridional configuration.

II. Condensed Phase Comprising an Amine

Embodiments of the disclosed integrated process include a condensed phase comprising an amine. In any of the following embodiments, the condensed phase may be an amine in a liquid state, a solution comprising an amine and a solvent in a liquid state, or a solid state (e.g., an amine supported on $SiO_2$). In some embodiments, the solvent is nonaqueous. The amine comprises a 1° amine group, a 2° amine group, a 3° amine group, or any combination thereof.

In any of the foregoing or following embodiments, the amine may comprise a polyamine, a tertiary amine, an alkanolamine, a diamine compound according to Formula I, or any combination thereof, the compound according to Formula I having a structure $R^1(R^2)N$-$L^1$-$NH$—$R^3$ where each of $R^1$ and $R^2$ independently is aliphatic or cycloaliphatic or $R^1$ and $R^2$ together with the nitrogen to which they are attached form a heterocyclyl ring, $L^1$ is aliphatic or cycloaliphatic or $L^1$ and $R^1$ together with the nitrogen to which they are attached form a heterocyclyl ring, and $R^3$ is aliphatic, cycloaliphatic, cycloalkylalkyl or alkoxyalkyl. In certain embodiments, the amine is not an amidine, since amidines may decompose under the reaction conditions.

In some embodiments, the condensed phase consists of the amine or consists essentially of the amine. By "consists essentially of" or "consists of" is meant that no additional solvent is affirmatively added to the amine. By "consists essentially of" is further meant that, prior to utilization in the integrated process, the condensed phase comprises at least 95 wt % of the amine. In other embodiments, the condensed phase is a solution comprising the amine and a solvent. In one embodiment, the solvent is a nonaqueous solvent. Exemplary nonaqueous solvents include, but are not limited to, alcohols (e.g., alkanols) and cyclic ethers (e.g., tetrahydrofuran). In an independent embodiment, the condensed phase is a solid state comprising the amine on a solid support.

In some embodiments, the condensed phase is a solution comprising a solvent and from 1 mol % to 95 mol % of a tertiary amine (with the remainder being the solvent), such as from 1 mol % to 75 mol %, 1 mol % to 50 mol %, 1 mol % to 20 mol %, 5 mol % to 20 mol %, or 5 mol % to mol % of the tertiary amine, or from 0.1 mol % to 2 mol % of a polyamine, such as from 0.2-1 mol % of the polyamine, or any combination thereof. In an independent embodiment, the condensed phase consists of or consists essentially of a polyamine or a compound according to Formula I.

In some embodiments, the amine is a polyamine. The polyamine may be, for example, a polyimine. In certain embodiments, the polyamine is polyethyleneimine (PEI) with a repeating unit of —[CH$_2$CH$_2$N(H)]$_n$— where n is an integer. The PEI may be linear or branched. Some branched PEIs are liquids including primary, secondary, and tertiary amino groups. One exemplary structure of a branched PEI having 1°, 2°, and 3° amine groups in an approximate ratio of 25:50:25 is shown below:

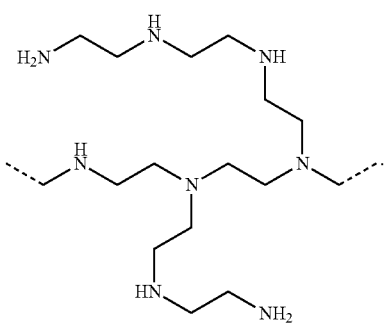

Liquid branched PEIs are soluble in water, lower alcohols (e.g., $C_1$-$C_5$ alcohols), glycols, and tetrahydrofuran (THF). In some embodiments, the PEI is a branched PEI. In certain embodiments, the branched PEI has a number average molecular weight $M_n$ within a range of from 500-250000 Da, such as from 500-10000 Da, 500-2000 Da, or 500-1000 Da. In any of the foregoing embodiments, the condensed phase may be a solution comprising the polyamine and a solvent. In some embodiments, the condensed phase comprises PEI and a nonaqueous solvent. In some examples, the condensed phase comprised branched PEI ($M_n$~600) and tetrahydrofuran.

In some embodiments, the amine is a tertiary amine. The tertiary amine may be, for example, a trialkylamine, a tertiary alkyl-substituted diamine, a tertiary alkanolamine, such as a dialkylalkanolamine, a tertiary cycloaliphatic amine, or a tertiary aromatic or heteroaromatic amine. In certain embodiments, the alkyl groups are $C_1$-$C_3$ alkyl groups. Exemplary tertiary amines include, but are not limited to, triethylamine, tetramethylethylenediamine, diethylethanolamine, N,N-diisopropylethylamine, 4-dimethylaminopyridine, and combinations thereof. In certain embodiments, the condensed phase is a solution comprising a trialkylamine and an alcohol. For example, the condensed phase may comprise triethylamine and ethanol. In some embodiments, the condensed phase comprises a trialkylamine and a $C_1$-$C_3$ alkanol in an amine:alkanol molar ratio of from 1:5 to 1:15, such as a molar ratio of from 1:8 to 1:12. In certain examples, the condensed phase comprised triethylamine and ethanol in a molar ratio of 1:10.

In some embodiments, the amine is a compound according to Formula I:

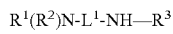

$R^1(R^2)N\text{-}L^1\text{-}NH\text{—}R^3$      Formula I.

Compounds according to Formula I also may referred to as carbon dioxide binding organic liquids ($CO_2BOLs$). With respect to Formula I, each of $R^1$ and $R^2$ independently is aliphatic, preferably alkyl, such as $C_{1-6}$alkyl, $C_{1-4}$alkyl, $C_{1-3}$alkyl, or $C_{1-2}$alkyl; cycloaliphatic, preferably cycloalkyl, such as $C_{3-7}$cycloalkyl or $C_{3-4}$cycloalkyl, and may be cyclopropyl; or $R^1$ and $R^2$ together with the nitrogen to which they are attached, form a heterocyclyl ring, such as an non-aromatic heterocyclyl ring, preferably a 5- or 6-membered heterocyclyl ring and optionally comprising one or more additional heteroatoms, such as 1 or 2 heteroatoms selected from oxygen, nitrogen or sulfur, and/or optionally substituted with alkyl, such as $C_{1-4}$alkyl. Alternatively, $R^1$ may form a heterocyclyl moiety, with $L^1$, such as a non-aromatic heterocyclyl moiety, preferably a 5- or 6-membered heterocyclyl moiety. In such embodiments, $R^2$ is aliphatic, preferably alkyl, such as $C_{1-6}$alkyl, $C_{1-4}$alkyl, $C_{1-3}$alkyl, or $C_{1-2}$alkyl, or cycloalkyl, such as $C_{3-7}$cycloalkyl.

In some embodiments, each of $R^1$ and $R^2$ independently is linear alkyl or branched alkyl, such as $C_{1-6}$linear alkyl, or $C_{3-6}$branched alkyl. Exemplary linear alkyl moieties include, but are not limited to methyl, ethyl, n-propyl or n-butyl, and exemplary branched alkyl moieties include, but are not limited to, isopropyl, tert-butyl, iso-butyl, or sec-butyl. And $R^1$ and $R^2$ may be the same or different. In other embodiments, $R^1$ and $R^2$ together with the nitrogen to which they are attached form a non-aromatic heterocyclyl moiety, such as morpholine, thiomorpholine, piperidine, pyrrolidine, or piperazine, optionally substituted with $C_{1-4}$alkyl, typically, methyl, ethyl, isopropyl, or tert-butyl.

$L^1$ is aliphatic, preferably alkyl, such as $C_{2-4}$alkyl or $C_{2-3}$alkyl; cycloaliphatic, preferably cycloalkyl, such as $C_{5-7}$cycloalkyl; or $L^1$ and $R^1$ together with the nitrogen to which they are attached form a non-aromatic heterocyclyl ring, such as a 5-, 6-, or 7-membered heterocyclyl, optionally comprising one or more additional heteroatoms, such as 1 or 2 heteroatoms selected from oxygen, nitrogen or sulfur. In some embodiments, $L^1$ is —$CH_2CH_2$— or —$CH_2CH_2CH_2$—, but in other embodiments, $L^1$ and $R^1$ together with the nitrogen to which they are attached, form a 5- or 6-membered non-aromatic heterocyclyl ring, such as a piperidine or pyrrolidine ring. In some such embodiments, $R^2$ is $C_{1-6}$alkyl, such as $C_{1-4}$alkyl, $C_{1-3}$alkyl, or $C_{1-2}$alkyl, preferably methyl or ethyl.

$R^3$ is aliphatic, cycloaliphatic, cycloalkylalkyl or alkoxyalkyl. In some embodiments, $R^3$ is alkyl, such as $C_{1-6}$alkyl, $C_{1-4}$alkyl, $C_{1-3}$alkyl, or $C_{1-2}$alkyl; cycloalkyl, such as $C_{3-7}$cycloalkyl or $C_{3-4}$cycloalkyl; cycloalkylalkyl, such as —$CH_2$cycloalkyl; or alkoxyalkyl, such as $C_{1-6}$alkyl, $C_{1-4}$alkyl, $C_{1-3}$alkyl, or $C_{1-2}$alkyl substituted $C_{1-4}$alkoxy, $C_{1-2}$alkoxy, or $C_{3-6}$cycloalkyl. $R^3$ may be linear or branched alkyl, and may be a linear $C_{1-6}$alkyl, $C_{1-4}$alkyl, $C_{1-3}$alkyl, or $C_{1-2}$alkyl or a branched $C_{3-6}$alkyl, $C_{3-4}$alkyl, or $C_3$alkyl. Exemplary linear and branched alkyl moieties include, but are not limited to, methyl, ethyl, n-propyl, or n-butyl, and isopropyl, isopropyl, tert-butyl, iso-butyl, or sec-butyl. In some embodiments, $R^3$ is unsubstituted, but in other embodiments, $R^3$ is substituted, and may be substituted with alkoxy, such as $C_{1-4}$alkoxy, or $C_{1-2}$alkoxy. Exemplary alkoxy substituents include, but are not limited to, methoxy, ethoxy, propoxy, isopropoxy or cycloalkoxy, such as cyclopropoxy.

Exemplary compounds within the scope of Formula I include:

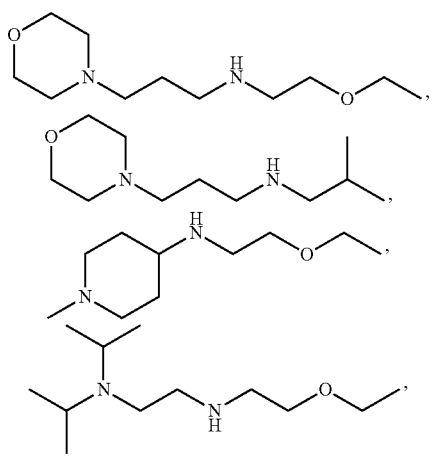

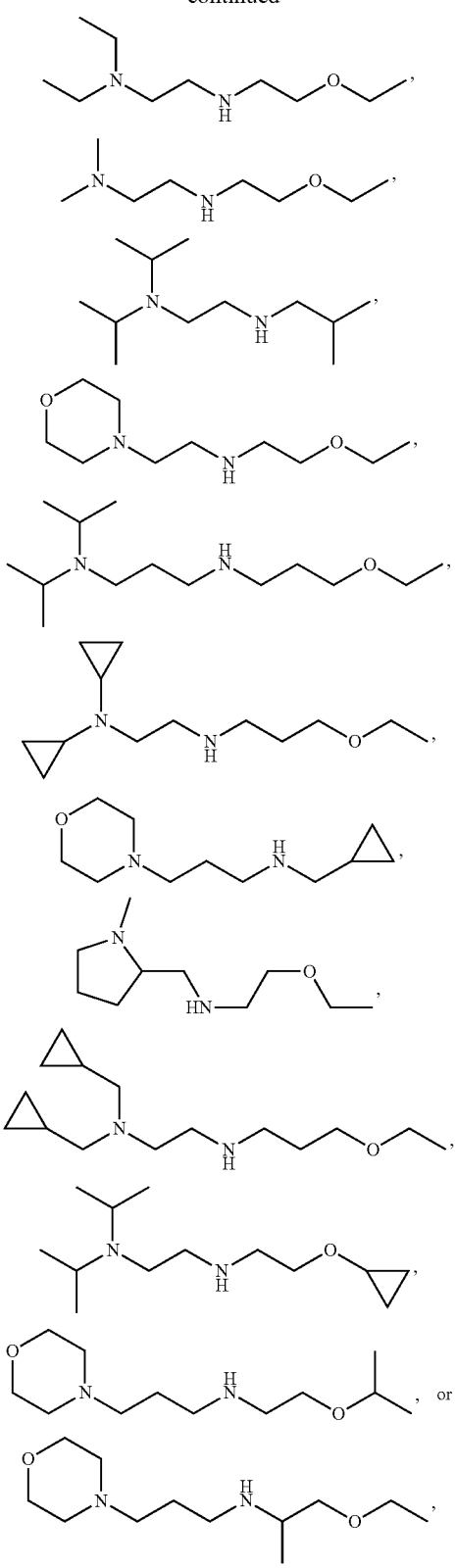

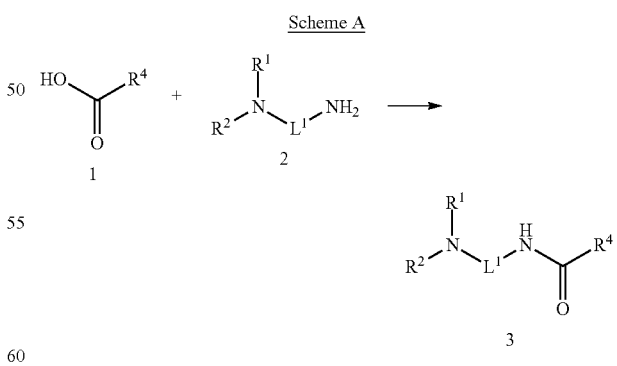

Formula II

Formula III    Formula IV

A person of ordinary skill in the art will understand that Formula II illustrates a zwitterionic state, while Formula IV illustrates the carbamic acid, and Formula III provides a potential intermediate state illustrating intramolecular bonding between the carbamate and the tertiary amine through the hydrogen. In some embodiments, when exposed to $CO_2$, the disclosed compounds form an equilibrium that comprises 50% or less of the zwitterionic form. The intramolecular H-bonding may shift the equilibrium toward a neutral form from the acid/base form. This in turn may reduce intermolecular bonding, which may help reduce the viscosity of the liquid, as the molecules can move more freely relative to each other. Additionally, limiting the compounds to a single hydrogen bond donor, such as a single secondary amine, also helps reduce the viscosity of the compound/$CO_2$ complex by reducing the intermolecular bonding between molecules.

Compounds according to Formula I may be prepared as exemplified below and as will be understood by a person of ordinary skill in the art or organic synthesis. With respect to the following exemplary reaction schemes, $R^1$, $R^2$, $R^3$ and $L^1$ are as defined herein, and $R^4$ is aliphatic, preferably alkyl, such as $C_{1-6}$alkyl, $C_{1-3}$alkyl, or $C_{1-2}$alkyl; cycloaliphatic, preferably cycloalkyl, such as $C_{3-7}$cycloalkyl or $C_{3-4}$cycloalkyl; or cycloalkylalkyl; or alkoxyalkyl, such that $R^4$ and the carbon to which it is attached together form $R^3$ as defined herein.

An exemplary synthesis may include the following first reaction step according to Scheme A.

Scheme A

Acid 1 activated by a suitable activating agent in a suitable solvent and treated with amine 2 to form amide 3. The activating agent may be any agent suitable to facilitate acid 1 coupling to amine 2. Suitable activating agents include, but are not limited to, boric acid; a carbodiimide reagent, such as 1-ethyl-3-(3-dimethylaminopropyl)carbodiimide Without being bound to a particular theory, when a compound according to Formula I disclosed herein is exposed to $CO_2$ it may exist in an equilibrium between Formulas II, III and IV, as shown below.

(EDC), or N,N'-dicyclohexylcarbodiimide (DCC), optionally in combination with hydroxybenzotriazole (HOBT); bis(2-oxo-3-oxazolidinyl)phosphinic chloride (BOP-Cl); thionyl chloride; mesyl chloride; tosyl chloride; or a combination thereof. Suitable solvents include, but are not limited to, aprotic solvents such as toluene, chlorinated solvents, such as chloroform or dichloromethane, dimethylformamide (DMF), tetrahydrofuran (THF), or a combination thereof. In some embodiments, the reaction may proceed with removal of water, such as by a drying agent or azeotropic water removal.

A second reaction step in the exemplary synthesis is provided below according to Scheme B.

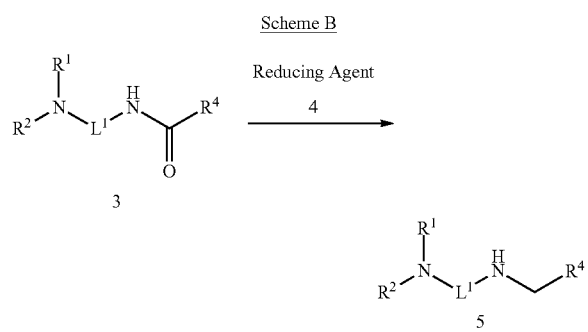

Amine 3 is treated with reducing agent 4 to form diamine 5. Reducing agent 4 can be any suitable reducing agent, such as lithium aluminum hydride, borane-dimethylsulfide, borane-THF, or lithium borohydride. And the reaction may be performed in a suitable solvent, such as THF, methanol, ether, or a combination thereof. And the reaction maybe performed at a temperature suitable to facilitate the reaction, such as from room temperature to reflux of the solvent.

Alternatively, compounds according to Formula I may be made by the synthesis illustrated by Scheme C.

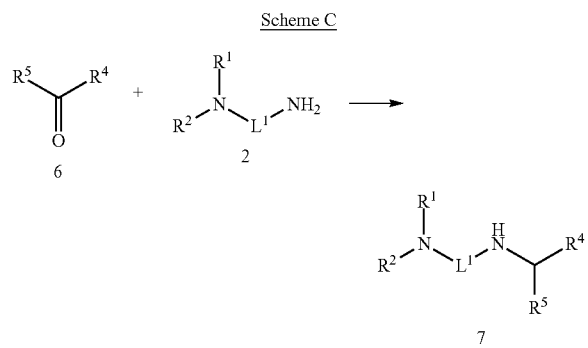

With respect to Scheme 3, $R^5$ is H or alkyl, such as $C_{1-6}$alkyl, $C_{1-4}$alkyl, ethyl, or methyl. Carbonyl compound 6 is treated with amine 2 and a reducing agent to form diamine 7. Suitable reducing agents are known to persons of ordinary skill in the art and may include, but are not limited to, borohydride reagents, such as sodium borohydride, sodium cyanoborohydride, sodium triacetoxyborohydride, or lithium borohydride, or catalytic reduction, such as by hydrogen with a palladium, nickel, ruthenium, or platinum catalyst, such as palladium on carbon. The reaction may be performed in one step, such as by reductive amination, or in two steps, where the amine and carbonyl compound are first allowed to react to form an imine, before being contacted by the reducing agent. A person of ordinary skill in the art will understand which solvent(s) are suitable for the particular reaction being performed, but suitable solvents may include alcohols, such as methanol, ethanol, or isopropanol, toluene, THF, acetonitrile, or a combination thereof.

Another exemplary synthesis suitable to produce the compounds according to Formula I is provided by Scheme D.

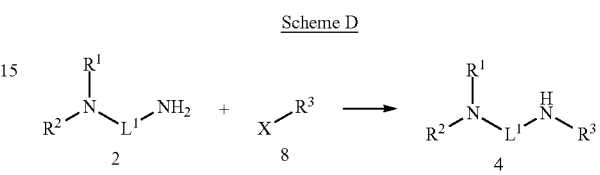

Amine 2 is treated with compound 8 to form compound 4. Typically, amine 2 is provided in excess, such as 2×, 3×, 4×, 5× or more excess with respect to compound 8, to facilitate the formation of compound 4, both to drive the reaction to completion and to limit formation of a tertiary amine. X is a suitable leaving group, such as, halogen, for example, bromo or chloro, methylate, or tosylate. The reaction may be performed neat, i.e., without an additional solvent, or alternatively, the reaction may be performed using a solvent. And the reaction may be performed in the presence or absence of an additionally added base. Suitable solvents include, but are not limited to, chlorinated solvents, such as chloroform or dichloromethane, toluene, acetonitrile, DMF, THF, pyridine or a combination thereof. And suitable bases include any base that will facilitate the reaction, such as a trialkylamine, for example, trimethylamine, pyridine, or an inorganic base, such as potassium carbonate. In some embodiments, the reaction mixture is contacted with an aqueous base to remove excess amine, and/or neutralize any salt of the product that may have formed. The reaction may be performed at a temperature suitable to facilitate the reaction, such as from 20° C. to 120° C. or more, or to reflux of the reactants and/or solvent, such as from 30° C. to 100° C., from 40° C. to 80° C., or from 40° C. to 60° C. In some embodiments, the reaction temperature is selected such that the reaction is performed in a condensed phase.

III. Hydrogenation Catalyst

A hydrogenation catalyst is used in embodiments of the disclosed integrated processes. The catalyst may be heterogeneous or homogeneous hydrogenation catalyst. Suitable catalysts may include, but are not limited to, those comprising Cu, Zn, Al, Pd, Pt, Si, Cr, Ru, Rh, Co, Ni, Zr, Ti, Ce, Mn, and combinations thereof. In some embodiments, the hydrogenation catalyst may comprise known materials to catalyze hydrogenation such (i) precious metals Pt, Pd, Rh, Ir, and Ru, base metals Ni, Co, Fe, Cu, and Zn, and catalysts supported on materials such as alumina, silica, carbon, and chromite and magnesium aluminum spinels, or any combination thereof; or (ii) a pincer ligand; or (iii) both (i) and (ii). Pincer ligands are often referred to as XYZ-type pincer ligands, where X, Y, and Z provide the identity of the coordinating atoms in the ligand. For example, a PNP pincer ligand chelates a metal atom via bonds with phosphorus, nitrogen, and phosphorus atoms of the ligand. Similarly, a PCP pincer ligand binds via phosphorus, carbon, and phosphorus. In certain embodiments, the pincer ligand is a NNP or PNP pincer. The pincer ligand backbone may be aromatic, heteroaromatic, aliphatic, or heteroaliphatic.

Suitable catalysts include, but are not limited to, Cu, ZnO, $Al_2O_3$, Pd, Pt, $SiO_2$, $Cu_2Cr_2O_5$, transition metal pincer-type catalysts (i.e., catalyst comprising one or more pincer ligands), and combinations thereof. In some embodiments, the transition metal pincer-type catalyst is a Ru-pincer catalyst. Two exemplary Ru-pincer catalysts are shown.

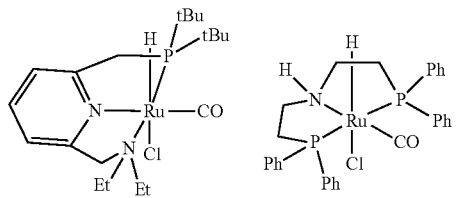

In some embodiments, the process is a conversion of $CO_2$ to methanol and water, and the catalyst comprises Cu, Zn, Al, or a combination thereof. In certain examples, the catalyst comprises $Cu/ZnO/Al_2O_3$.

In some embodiments, the process is a conversion of $CO_2$ to methanol and a glycol, and the catalyst is a Ru-based catalyst. In certain embodiments, the Ru-based catalyst is a Ru-pincer catalyst, such as

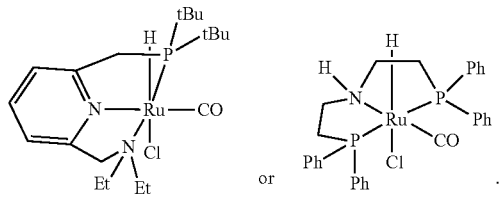

IV. Process for Producing Methanol

In some embodiments, an integrated process for capture and conversion of $CO_2$ to methanol includes combining the $CO_2$, a hydrogenation catalyst, and hydrogen with a condensed phase comprising an amine under conditions effective to form methanol and water. The methanol and water are separated from the amine, and subsequently from one another. The overall process is $CO_2 + 3H_2 \rightarrow CH_3OH + H_2O$, $\Delta H = -49.4$ kJ/mol. In some embodiments, the reaction proceeds via formamide or formate ester intermediates in the condensed phase. In certain embodiments, after the methanol and water are separated, the methanol has a purity within a range of 99-99.9%, such as a purity of 99.5-99.8%.

In any of the foregoing or following embodiments, prior to combination with the $CO_2$, hydrogenation catalyst, and hydrogen, the condensed phase may comprise, consist of, or consist essentially of the amine. In one embodiment, the condensed phase consists of the amine. The condensed phase may consist of the amine when the amine is a liquid at ambient temperature or under the conditions at which the amine and $CO_2$ are combined. In an independent embodiment, the condensed phase consists essentially of the amine. In another independent embodiment, the condensed phase is a solution comprising the amine and a nonaqueous solvent. In still another embodiment, the condensed phase comprises the amine and from 0-10 wt % water, such as from 0-5 wt % water or 0-2 wt % water. In some examples, the condensed phase is substantially devoid of water prior to the conversion of $CO_2$ to methanol, e.g., the condensed phase prior to reaction may comprise less than 1 wt % water, prior to reaction.

In any of the foregoing or following embodiments, the condensed phase comprises an amine as previously discussed. In some embodiments, the condensed phase is a solution comprising a solvent and a tertiary amine. The solvent may be an alcohol. Suitable tertiary amines include, but are not limited to, trialkylamines. In some examples, the amine is triethylamine and the alcohol is an alkanol, e.g., ethanol. In certain working embodiments, the condensed phase comprised triethylamine:ethanol in a 1:10 molar ratio.

In any of the foregoing or following embodiments, the amine may be a compound according to Formula I, i.e., a $CO_2BOL$. In certain embodiments, the condensed phase consists of or consists essentially of the $CO_2BOL$. By "consists essentially of" or "consists of" is meant that no additional solvent is affirmatively added to the $CO_2BOL$. By "consists essentially of" is further meant that, prior to $CO_2$ capture and conversion, the condensed phase comprises at least 95 wt % of the $CO_2BOL$ and comprises less than 1 wt % of any other amine. The condensed phase may be substantially devoid of water prior to the conversion of $CO_2$ to methanol, e.g., the condensed phase prior to reaction may comprise less than 5 wt % water, such as less than 1 wt % water, prior to reaction. The absence of a cosolvent in some embodiments maximizes the amine concentration and/or the concentration of captured $CO_2$, and concomitantly reduces the volume of the condensed phase and the energy required to heat the condensed phase to a desired temperature for $CO_2$ capture and subsequent conversion. The absence of a cosolvent also may simplify the downstream solvent separation and recovery unit.

In any of the foregoing or following embodiments, the hydrogenation catalyst may comprise known materials to catalyze hydrogenation such (i) precious metals Pt, Pd, Rh, Ir, and Ru, base metals Ni, Co, Fe, Cu, and Zn, and catalysts supported on materials such as alumina, silica, carbon, and chromite and magnesium aluminum spinels, or any combination thereof; or (ii) a pincer ligand; or (iii) both (i) and (ii). In some embodiments, the hydrogenation catalyst comprises a copper-containing catalyst, a zinc-containing catalyst, an aluminum-containing catalyst, or any combination thereof. In certain embodiments, the hydrogenation catalyst comprises $Cu/ZnO/Al_2O_3$.

FIG. 1 shows one exemplary embodiment of an integrated process for converting $CO_2$ to methanol. $CO_2$, a hydrogenation catalyst, hydrogen, and a condensed phase comprising an amine are combined (110). The combined components are subjected to an effective temperature $T_M$ and initial pressure $P_M$ for a sufficient time $t_M$ to form a solution comprising $CH_3OH$, $H_2O$, and the condensed phase amine (120). In this step, carbon dioxide is captured by the amine in the condensed phase and is then hydrogenated to form methanol and water. By "captured" is meant that the $CO_2$ is adsorbed, absorbed, covalently bound (e.g., in the form of an alkylcarbonic acid or alkylcarbamic acid), or ionically bound to the amine in the condensed phase. In some embodiments, $CO_2$ capture is performed at a temperature $\leq 60°$ C., such as a temperature within a range of 25-60° C. In certain embodiments where $T_M > 60°$ C., a period of time is allowed for $CO_2$ capture before increasing the temperature to $T_M$. A separation is performed to provide a solution comprising $CH_3OH$ and $H_2O$ (130) and the condensed phase amine (140), which optionally is recycled and reused. The separation may be performed by any suitable method. In some embodiments, a flash separation may be performed. For example, a flash drum may be used to separate methanol and water vapor from the condensed phase amine. In another example, a distillation column may be used when the condensed phase amine has a boiling point close to that of methanol or water. The $CH_3OH$ and $H_2O$ are then separated to provide $CH_3OH$ (150) and $H_2O$ (160). In some embodiments, the $CH_3OH$ and $H_2O$ are separated by distillation.

In contrast to other methods utilizing gas-phase $CO_2$ hydrogenation, embodiments of the disclosed process provide $CO_2$ hydrogenation in the condensed phase. Additionally, no mechanical compression of the $CO_2$ is needed for transport. Advantageously, the $CO_2$ hydrogenation process is exothermic, which partially offsets the energy required for $CO_2$ capture and subsequent separation of the methanol and water vapor from the condensed phase amine. Moreover, in some embodiments, the amine synergistically acts as a co-catalyst for the hydrogenation reaction by charge stabilizing the captured $CO_2$ in the form of charged/polar intermediates as discussed in more detail below. In some embodiments, the disclosed process reduces capital and operating costs by at least 20% relative to a benchmark methanol synthesis via gas-phase $CO_2$ hydrogenation.

In any of the foregoing embodiments, the temperature $T_M$ may be within a range of from 50° C. to 180° C., such as from 100° C. to 180° C., 110-170° C., 120-150° C., or 120-130° C. In any of the foregoing embodiments, the initial pressure $P_M$ may be within a range of from 1 MPa to 10 MPa. In some embodiments, the initial pressure is from 1-6 MPa, 2-5 MPa, or 2-4 MPa. In contrast, conventional syngas conversion technologies are performed at temperatures ranging from 250-300° C. and pressures ranging from 5-10 MPa. Advantageously, in some embodiments, the lower temperature of the disclosed process favors the exothermic formation of $CH_3OH$ over the endothermic reverse water gas shift reaction ($CO_2+H_2 \rightarrow CO+H_2O$, $\Delta H=+41.1$ kJ/mol), thereby increasing selectivity for methanol formation. In any of the foregoing embodiments, the time $t_M$ may be within a range of from 3 seconds to 36 hours, such as from 15 seconds to 36 hours, 30 seconds to 36 hours, 1 minute to 36 hours, 5 minutes to 36 hours, 10 minutes to 36 hours, 30 minutes to 36 hours, 1-36 hours, 3-36, 6-24 hours, 12-18 hours, 3 seconds to 3 hours, 3 seconds to 1 hour, 5 seconds to 1 hour, 10 seconds to 30 minutes, or 15 seconds to 15 minutes. In a continuous process, the time $t_M$ may be on the order of a few seconds to several minutes, whereas the time $t_M$ may be on the order of several hours in a batch process. As set forth above, in certain embodiments where $T_M>60°$ C., a period of time is allowed for $CO_2$ capture before increasing the temperature to $T_M$. The period of time for initial $CO_2$ capture may range from a few seconds to several hours, with longer times being used in batch processes.

In some embodiments, the conversion of $CO_2$ to methanol is a one-pot, one-step process as shown in FIG. 1, where $CO_2(g)$ and $H_2(g)$ are combined with the hydrogenation catalyst and a condensed phase amine in a vessel and subjected to effective conditions for the reaction to occur. The hydrogenation catalyst may be disposed in a fixed bed or a fluidized bed. In any of the foregoing embodiments, the condensed phase amine may be an amine-containing solvent, a solution comprising the amine and a solvent, or a solid state (e.g., an amine supported on $SiO_2$).

In an independent embodiment, the $CO_2$ is present in the condensed phase with the amine prior to combination with hydrogen and the hydrogenation catalyst. In certain examples, the conversion of $CO_2$ to methanol is a two-step process. As shown in FIG. 2, $CO_2$ is combined with a condensed phase amine (202) under effective conditions to form a condensed phase comprising the amine, the $CO_2$, and optionally a solvent (204). The effective conditions include a temperature T', an initial pressure P', and time t' sufficient for the condensed phase amine to capture $CO_2$, thereby providing a condensed phase comprising the amine and captured $CO_2$. In other embodiments, the process may commence with a condensed phase comprising the amine and captured $CO_2$ (204). The condensed phase comprising the amine and $CO_2$ is combined with $H_2$ and the hydrogenation catalyst (210). The combined components are subjected to an effective temperature $T_M$ and initial pressure $P_M$ for a sufficient time $t_M$ to form a solution comprising $CH_3OH$, $H_2O$, and the condensed phase amine (220), where $T_M$, $P_M$, and $t_M$ are as described above. A separation is performed to provide a solution comprising $CH_3OH$ and $H_2O$ (230) and the condensed phase amine (240), which optionally is recycled and reused. The separation may be performed by any suitable method as set forth above. The $CH_3OH$ and $H_2O$ are then separated to provide $CH_3OH$ (250) and $H_2O$ (260). In some embodiments, the $CH_3OH$ and $H_2O$ are separated by distillation.

In any of the foregoing or following embodiments, the temperature T' may be within a range of from 20° C. to 60° C., such as from 25-50° C. In some embodiments, T' is ambient temperature, e.g., 20-30° C. In any of the foregoing embodiments, the initial pressure P' may be within a range of from 0.1 MPa to 5 MPa, such as an initial pressure within a range of from 0.1-2 MPa or 0.1-1 MPa. In any of the foregoing embodiments, the $CO_2$ capture may be substantially immediate. In some embodiments, the time t' is within a range of from greater than zero seconds to 36 hours, such as from 3 seconds to 36 hours, 15 seconds to 36 hours, 30 seconds to 36 hours, 1 minute to 36 hours, 5 minutes to 36 hours, 10 minutes to 36 hours, 30 minutes to 36 hours, 1-36 hours, 3-36, 6-24 hours, 12-18 hours, 3 seconds to 3 hours, 3 seconds to 1 hour, 5 seconds to 1 hour, 10 seconds to 30 minutes, or 15 seconds to 15 minutes. In a continuous process, the time t' may be on the order of a few seconds to several minutes, whereas the time t' may be on the order of several hours in a batch process.

In any of the foregoing or following embodiments, the amine may be a tertiary amine or a diamine (e.g., a compound according to Formula I), and the amine and $CO_2$ may be combined in a molar ratio of from 1:4 to 10:1, such as from 1:2 to 5:1 or 1:1 to 5:1. Alternatively, the amine may be a polyamine, and the polyamine and $CO_2$ may be combined in a molar ratio of from 1:25 to 1:300, such as from 1:50 to 1:150.

In any of the foregoing or following embodiments, the $H_2$ may be in stoichiometric excess relative to the $CO_2$. Excess $H_2$ shifts the reaction equilibrium and increases $CO_2$ to methanol conversion. The stoichiometric $H_2$:$CO_2$ ratio for reaction in the condensed phase is 3:1. In some embodiments, the amine present in the condensed phase is the limiting reagent such that not all of the $CO_2$ is captured by the amine, and the amount of $H_2$ added is in stoichiometric excess relative to amount of $CO_2$ in the condensed phase, e.g., $CO_2$ captured by the amine in the condensed phase. In certain embodiments, the process is performed with a molar ratio of added $H_2$ to $CO_2$ from 2:1 to 10:1, such as from 4:1 to 6:1, providing a molar ratio of $H_2$ to $CO_2$ in the condensed phase of from greater than 3:1 to 10:1. Excess $H_2$ may be recycled as shown in FIGS. 1 and 2.

In any of the foregoing or following embodiments, $CO_2$ captured by the amine may be the limiting reactant, and at least 25 mol %, at least 50 mol %, at least 75 mol %, at least 90 mol %, or even at least 95 mol % of the captured $CO_2$ is consumed. For example, from 25-100, 50-100, 75-100, 90-100, or 95-100 mol % of the captured $CO_2$ may be consumed. Alternatively, at least 10 mol %, at least 25 mol %, at least 50 mol %, or at least 75 mol % of $CO_2$ combined with the hydrogen, hydrogen catalyst, and condensed phase comprising the amine is consumed. For example, from 10-100, 25-100, 50-100, or 75-100 mol % of the $CO_2$ may be consumed.

Figure 3A:
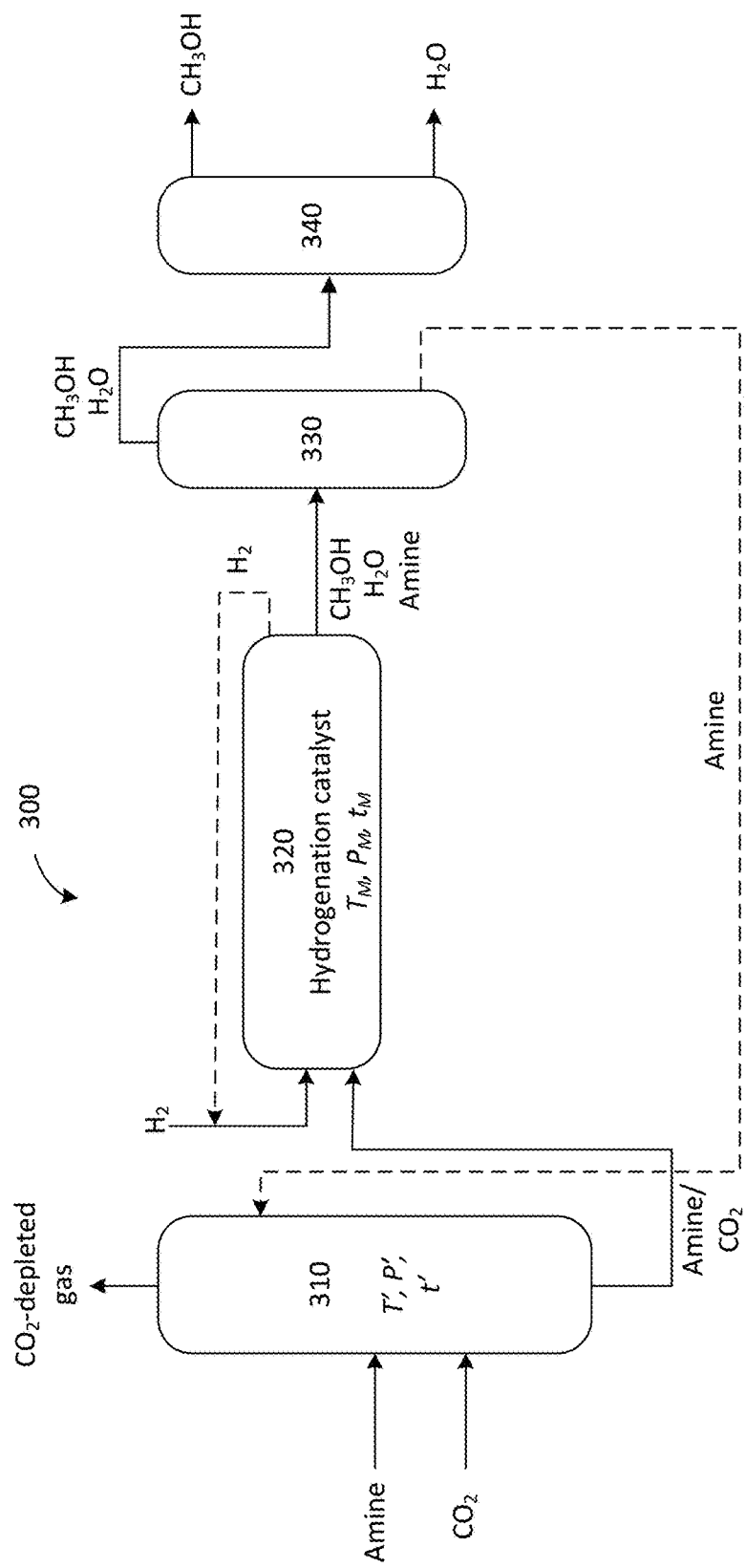
FIGS. 3A and 3B are simplified schematic diagrams of an exemplary apparatus for performing the process of FIG. 2.
Figure 3B:
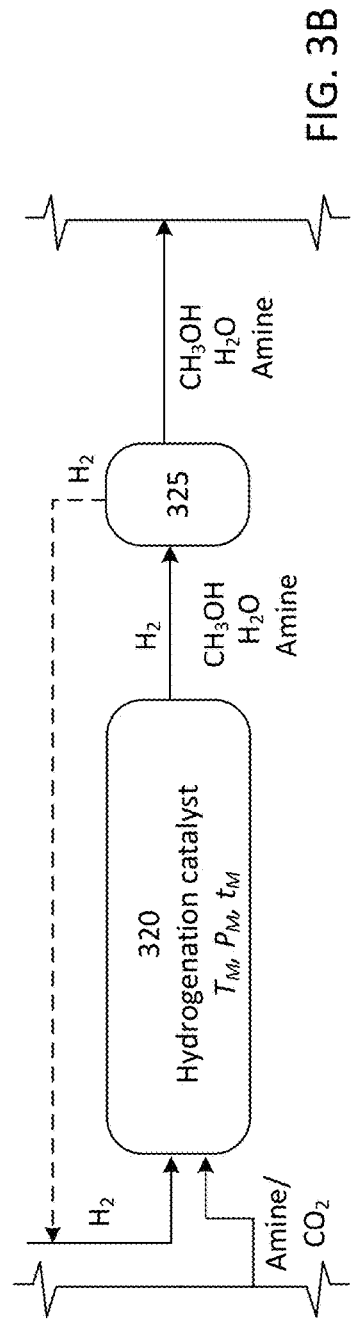

FIG. 3A is a schematic diagram of one embodiment of an apparatus 300 for performing the method of FIG. 2. A condensed phase comprising an amine and a gas flow comprising $CO_2$ are flowed into a $CO_2$ absorber 310. The condensed phase comprising the amine and the $CO_2$ are subjected to a temperature T', an initial pressure P', and time t' sufficient for the amine to capture the $CO_2$ to form a condensed phase solution comprising the amine and $CO_2$. A $CO_2$-depleted gas is exhausted from the $CO_2$ absorber 310. The condensed phase solution flows into a hydrogenation reactor 320 where it is combined with $H_2$ and a hydrogenation catalyst disposed within the hydrogenation reactor 320. In any of the foregoing embodiments, the hydrogenation catalyst may be disposed in a fixed bed or a fluidized bed within the hydrogenation reactor 320. If the bed is a fluidized bed, the $H_2$ flow and/or the condensed phase solution may be used for the fluidization. The combined components are subjected to an effective temperature $T_M$ and initial pressure $P_M$ for a sufficient time $t_M$ to form a condensed phase solution comprising $CH_3OH$, $H_2O$, and the amine. In any of the foregoing embodiments, the condensed phase solution, the hydrogen, or both may be pre-heated to a temperature ranging from greater than ambient to $T_M$ before entering the hydrogenation reactor. In some embodiments, the $H_2$ flowing into the hydrogenation reactor 320 is in stoichiometric excess relative to the $CO_2$ in the condensed phase, and excess $H_2$ exiting the hydrogenation reactor optionally is recycled back into the hydrogenation reactor. Excess $H_2$ shifts the reaction equilibrium and increases $CO_2$ to methanol conversion. In certain embodiments, e.g., as shown in FIG. 3B, the excess $H_2$ and the condensed phase solution comprising the $CH_3OH$, $H_2O$, and amine exiting the hydrogenation reactor 320 are flowed into a separator 325 where the $H_2$ is separated from the solution and subsequently recycled to the hydrogenation reactor 320. The $H_2$ and the condensed phase solution may be cooled, e.g., to 30-50° C. before entering the separator 325. In some embodiments, the separator 325 is a flash drum, such as a low-temperature flash drum operating at a temperature of 20-50° C., such as 30-50° C., and a pressure of 1-5 MPa, such as 2-3 MPa. The condensed phase solution comprising the $CH_3OH$, $H_2O$, and the amine exiting the hydrogenation reactor 320 (or separator 325) is flowed into a separator 330 where the condensed phase amine is separated from the $CH_3OH$ and $H_2O$. In some embodiments, the separator 330 is a flash drum or a distillation column. In certain embodiments, the separator 330 is a flash drum operating at a temperature within a range of from 100-150° C., such as 120-140° C., and a pressure of 0.1-1 MPa, such as 0.1-0.5 MPa. The condensed phase amine optionally is recycled back to the $CO_2$ absorber 310. The $CH_3OH$ and $H_2O$ are flowed into a distillation column 340 where the $CH_3OH$ and $H_2O$ are separated.

In any of the foregoing embodiments, the process may be a batch process or a continuous process. Some embodiments of the apparatus shown in FIGS. 3A and 3B may be suitable for a continuous process. In a continuous process, the hydrogenation catalyst may be disposed in a fixed bed in the hydrogenation reactor 320, and both $H_2$ and the condensed phase solution comprising the amine and $CO_2$ flow through or across the fixed bed. Alternatively, the hydrogenation catalyst may be disposed in a fluidized bed in the hydrogenation reactor 320, where the bed is fluidized by the $H_2$ flow and/or the condensed phase solution, and the $H_2$ and the condensed phase solution comprising the amine and $CO_2$ flow through the fluidized bed. In some embodiments, the condensed phase solution is flowed through the hydrogenation reactor at a space velocity of from greater than 0 to 50,000 $hr^{-1}$, such as from 1-50,000, 100-50,000, 500-40,000, 500-30,000, or 1,000-25,000 $hr^{-1}$. In some embodiments, a lower space velocity provides an increased conversion of $CO_2$ to methanol.

In an exemplary embodiment, $CO_2$ is combined with a condensed phase comprising triethylamine and ethanol (1:10 molar ratio, e.g., 2 mmol triethylamine and 20 mmol ethanol), a hydrogenation catalyst (e.g., $Cu/ZnO/Al_2O_3$) and excess hydrogen relative to an amount of the $CO_2$ captured by the amine in the condensed phase. The combined components are heated to 170° C. for 16-24 h, thereby converting $CO_2$ to methanol and water.

V. Process for Coproducing Methanol and a Glycol

Industrially, methanol is produced from a syngas mixture in the presence of a Cu-based catalyst at high temperature and high pressure. The reaction byproduct, water, is separated from the methanol by distillation and is not further utilized, which reduces the net atom efficiency. Glycols typically are produced by hydrolysis of epoxides in excess water under acidic conditions at high temperatures (>150° C.). In addition, the hydrolysis product stream is often contaminated with glycol oligomers, resulting in an energy penalty associated with separating glycol(s) from water and the oligomers.

Disclosed herein is an integrated process for capture and conversion of $CO_2$ to methanol and a glycol that concurrently produces a 1:1 mixture of methanol and the glycol. Advantageously, the process does not require addition of water. Instead, water is formed in situ and immediately consumed. In some embodiments, the disclosed process includes combining an epoxide, a hydrogenation catalyst, hydrogen, and $CO_2$ with a condensed phase comprising an amine under conditions effective to form methanol and a glycol. In any of the foregoing or following embodiments, the reactants may consist of, or consist essentially of, the epoxide, the hydrogenation catalyst, hydrogen, $CO_2$, and the condensed phase. In such embodiments, water is not added as a reactant. In this context, "consists essentially of" means that the reactants include no more than trace amounts (e.g., less than 0.5 wt %) water and other components that may participate in the reaction are excluded. Overall, the net reaction is:

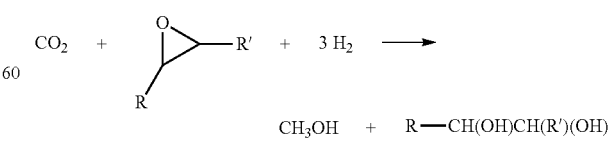

where R and R' independently are H or aliphatic, or R and R' together with the carbon atoms to which they are attached form a cycloaliphatic ring. By varying R and R' on the epoxide, different glycols can be made. In some embodiments, R and R' independently are H or $C_1$-$C_{10}$ alkyl. In an independent embodiment, R is H or $C_1$-$C_{10}$ alkyl and R' is H. In certain embodiments, R is H, methyl, or ethyl, and R' is H. In particular examples, R is methyl and R' is H such that the epoxide is propylene oxide and the resulting glycol is propylene glycol. In another independent embodiment, R and R' together with the carbon atoms to which they are attached form a cycloaliphatic ring. In one non-limiting example, the epoxide is cyclohexene oxide (also known as 1,2-epoxycyclohexane or 7-oxabicyclo[4.1.0]heptane) and the resulting glycol is cyclohexane-1,2-diol:

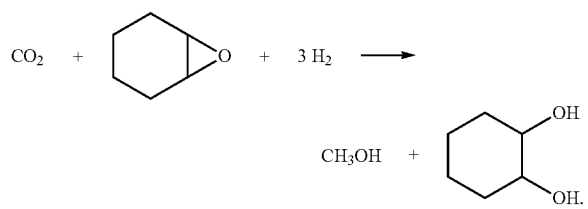

By combining both syntheses in a single process, the energy intensive separations associated with the individual processes are avoided. Instead, the byproduct from one reaction is the feed for another reaction. Additionally, the unique reactivity of the $CO_2$ captured by the amine (i.e., the nucleophilicity of the anionic "captured" $CO_2$ as an alkylcarbonate or alkylcarbamate) is exploited to open the epoxide ring, forming a cyclic carbonate, which is then hydrogenated to produce methanol and glycol at the same time. In some embodiments, the process exhibits 100% atom efficiency with no waste.

In any of the foregoing or following embodiments, prior to combination with the $CO_2$, epoxide, hydrogenation catalyst, and hydrogen, the condensed phase may comprise, consist of, or consist essentially of the amine. In one embodiment, the condensed phase consists of the amine. The condensed phase may consist of the amine when the amine is a liquid at ambient temperature or under the conditions at which the amine and $CO_2$ are combined. In an independent embodiment, the condensed phase consists essentially of the amine. In another independent embodiment, the condensed phase is a solution comprising the amine and a nonaqueous solvent. In still another embodiment, the condensed phase comprises the amine and from 0-10 wt % water, such as from 0-5 wt % water or 0-2 wt % water. In some examples, the condensed phase is substantially devoid of water prior to the conversion of $CO_2$ to methanol, e.g., the condensed phase prior to reaction may comprise less than 1 wt % water, prior to reaction.

The condensed phase comprises an amine. In some embodiments, the amine is a polyamine or a compound according to Formula I as previously discussed. In certain embodiments, the amine is a polyamine, such as polyethyleneimine (PEI). In some examples, the amine is a branched PEI with a molecular weight, $M_n$, within a range of 500-2,000 g/mole. In some embodiments, the condensed phase comprises PEI and a nonaqueous solvent. In certain examples, the amine is branched PEI and the nonaqueous solvent is tetrahydrofuran. In an independent embodiment, the condensed phase consists of, or consists essentially of, a compound according to Formula I.

In any of the foregoing or following embodiments, the amine may be a polyamine, and the polyamine and $CO_2$ may be combined in a molar ratio of from 1:5 to 1:300, such as from 1:25 or 1:250 or 1:50 to 1:150. Alternatively, the amine may be a tertiary amine or a diamine (e.g., a compound according to Formula I), and the amine and $CO_2$ may be combined in a molar ratio of from 1:4 to 10:1, such as from 1:2 to 5:1 or 1:1 to 5:1.

In any of the foregoing or following embodiments, the hydrogenation catalyst may comprise known materials to catalyze hydrogenation such (i) precious metals Pt, Pd, Rh, Ir, and Ru, base metals Ni, Co, Fe, Cu, and Zn, and supported on materials such as alumina, silica, carbon, and chromite and magnesium aluminum spinels, or any combination thereof; or (ii) a pincer ligand; or (iii) both (i) and (ii). In some embodiments, the hydrogenation catalyst comprises a ruthenium-based catalyst, such as a ruthenium-pincer catalyst. In certain embodiments, the hydrogenation catalyst is:

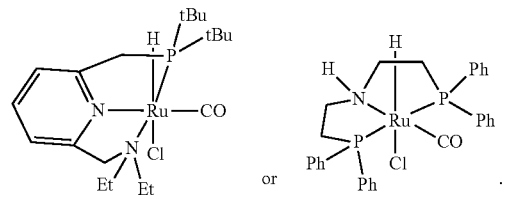

In any of the foregoing or following embodiments, the stoichiometric $H_2$:$CO_2$ ratio for reaction in the condensed phase is 3:1. In some embodiments, the amine present in the condensed phase is the limiting reagent such that not all of the $CO_2$ is captured by the amine, and the amount of $H_2$ added is in stoichiometric excess relative to amount of $CO_2$ in the condensed phase, e.g., $CO_2$ captured by the amine in the condensed phase. In certain embodiments and the amount of $H_2$ added is in stoichiometric excess relative to amount of $CO_2$ in the condensed phase, e.g., $CO_2$ captured by the amine in the condensed phase. In some embodiments, the process is performed with a molar ratio of added $H_2$ to $CO_2$ from 2:1 to 10:1, such as from 4:1 to 6:1, providing a molar ratio of $H_2$ to $CO_2$ in the condensed phase of from greater than 3:1 to 10:1.

In any of the foregoing or following embodiments, at least 10 mol % of the epoxide may be consumed in the reaction. In some embodiments, the epoxide is a limiting reactant and at least 25 mol %, at least 50 mol %, at least 75 mol %, at least 90 mol %, or even at least 95 mol % of the epoxide is consumed. For example, from 25-100, 50-100, 75-100, 90-100, or 95-100 mol % of the epoxide may be consumed.

Alternatively, $CO_2$ captured by the amine may be the limiting reactant, and at least mol %, at least 50 mol %, at least 75 mol %, at least 90 mol %, or even at least 95 mol % of the captured $CO_2$ is consumed. For example, from 25-100, 50-100, 75-100, 90-100, or 95-100 mol % of the captured $CO_2$ may be consumed. In another alternative, at least 10 mol %, at least 25 mol %, at least 50 mol %, or at least 75 mol % of $CO_2$ combined with the epoxide, hydrogen, hydrogen catalyst, and condensed phase comprising the amine is consumed. For example, from 10-100, 25-100, 50-100, or 75-100 mol % of the $CO_2$ may be consumed.

FIG. 4 shows one exemplary embodiment of the process. The $CO_2$, an epoxide, a hydrogenation catalyst, and hydrogen are combined with a condensed phase comprising an amine and optionally a solvent (410). The combined components are subjected to an effective temperature $T_{MG}$ and initial pressure $P_{MG}$ for a sufficient time $t_{MG}$ to form a solution comprising $CH_3OH$, glycol, and the condensed phase comprising the amine (420). One possible mechanism for the reaction is shown in exemplary Scheme 1 below where the epoxide is propylene oxide PO. Carbon dioxide is captured by the amine in the condensed phase and reacts with the epoxide to form a cyclic carbonate (propylene carbonate PC, Step (a)). The cyclic carbonate is hydrogenated and proceeds through Intermediates A-C to form the glycol and formamide (Steps i-iv). Steps ii and iv are equilibria. The formamide obtained in Step iv is further hydrogenated to form methanol (Step v).

Scheme 1

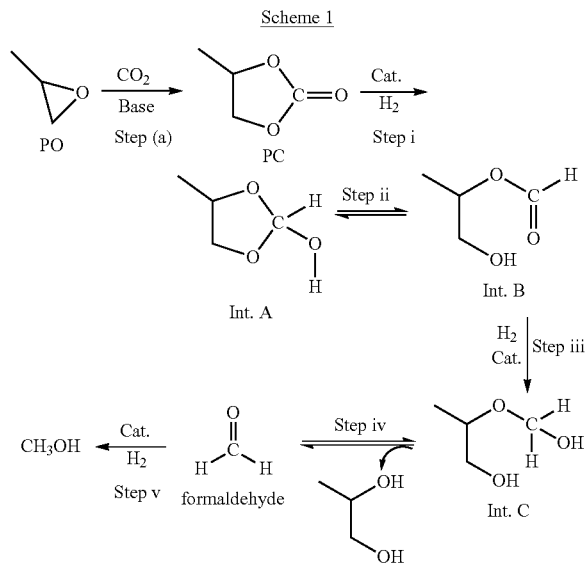

A separation is performed to provide (i) CH$_3$OH (430) and (ii) a solution comprising glycol and the condensed phase comprising the amine (440). The separation may be performed by any suitable method. In some embodiments, the solution is cooled, e.g., to a temperature within a range of from −100° C. to 30° C. prior to separating the methanol from the condensed phase. In certain embodiments, a flash and/or distillation separation may be performed. For example, a flash drum may be used to separate methanol from the glycol and the condensed phase comprising the amine. The solution comprising glycol and the condensed phase 440 may be separated by distillation to provide the condensed phase comprising the amine (450) and the glycol (460). The condensed phase comprising the amine (450) is optionally recycled and reused. In some examples, the CH$_3$OH and glycol may be removed together from the amine, and the CH$_3$OH and glycol are then separated, e.g., by distillation (not shown).

In any of the foregoing embodiments, the temperature $T_{MG}$ may be within a range of from 50° C. to 170° C., such as from 100° C. to 170° C., 120-160° C. or 130-150° C. In any of the foregoing embodiments, the initial pressure $P_{MG}$ may be within a range of from 3 MPa to 10 MPa. In some embodiments, the initial pressure is from 3-7 MPa or 5-7 MPa. In any of the foregoing embodiments, the time $t_{MG}$ may be within a range of from 3 seconds to 36 hours, such as from 15 seconds to 36 hours, 30 seconds to 36 hours, 1 minute to 36 hours, 5 minutes to 36 hours, 10 minutes to 36 hours, 30 minutes to 36 hours, 1-36 hours, 3-36, 6-24 hours, 12-18 hours, 3 seconds to 3 hours, 3 seconds to 1 hour, 5 seconds to 1 hour, 10 seconds to 30 minutes, or 15 seconds to 15 minutes. In a continuous process, the time $t_{MG}$ may be on the order of a few seconds to several minutes, whereas the time $t_{MG}$ may be on the order of several hours in a batch process. In certain embodiments where $T_{MG}>60°$ C., a period of time is allowed for CO$_2$ capture before increasing the temperature to $T_{MG}$. The period of time for initial CO$_2$ capture may range from a few seconds to several hours, with longer times being used in batch processes.

In an independent embodiment, the CO$_2$ is present in the condensed phase comprising the amine prior to combining the condensed phase with the epoxide, hydrogenation catalyst, and hydrogen. In such embodiments, the condensed phase is a solution comprising the amine, CO$_2$, and optionally a solvent. As shown in FIG. 5, the process optionally includes combining CO$_2$ with a condensed phase comprising the amine (502) under effective conditions to form a condensed phase comprising the amine, the CO$_2$, and optionally a solvent (504). The effective conditions include a temperature T', an initial pressure P', and time t' sufficient for the condensed phase amine to capture CO$_2$, thereby providing a condensed phase comprising the amine and captured CO$_2$. The temperature T', initial pressure P', and time t' are as previously described. In other embodiments, the process may commence with a condensed phase comprising the amine and captured CO$_2$ (504). The condensed phase comprising the amine and CO$_2$ is combined with the epoxide, the hydrogenation catalyst, and hydrogen (510). The combined components are subjected to an effective temperature $T_{MG}$ and initial pressure $P_{MG}$ for a sufficient time $t_{MG}$ to form a solution comprising CH$_3$OH, glycol, and the condensed phase comprising the amine (520), where $T_{MG}$, $P_{MG}$, and $t_{MG}$ are as described above. A separation is performed to provide CH$_3$OH (530) and a solution comprising glycol and the condensed phase comprising the amine (540). The separation may be performed by any suitable method. In some embodiments, a flash separation or distillation may be performed by any suitable method as set forth above. The glycol and the condensed phase comprising the amine are then separated (e.g., by distillation) to provide the condensed phase comprising the amine (550) and glycol (560). The condensed phase comprising the amine (550) is optionally recycled and reused. In some examples, the CH$_3$OH and glycol may be removed together from the amine, and the CH$_3$OH and glycol are then separated, e.g., by distillation (not shown).

Figure 6:
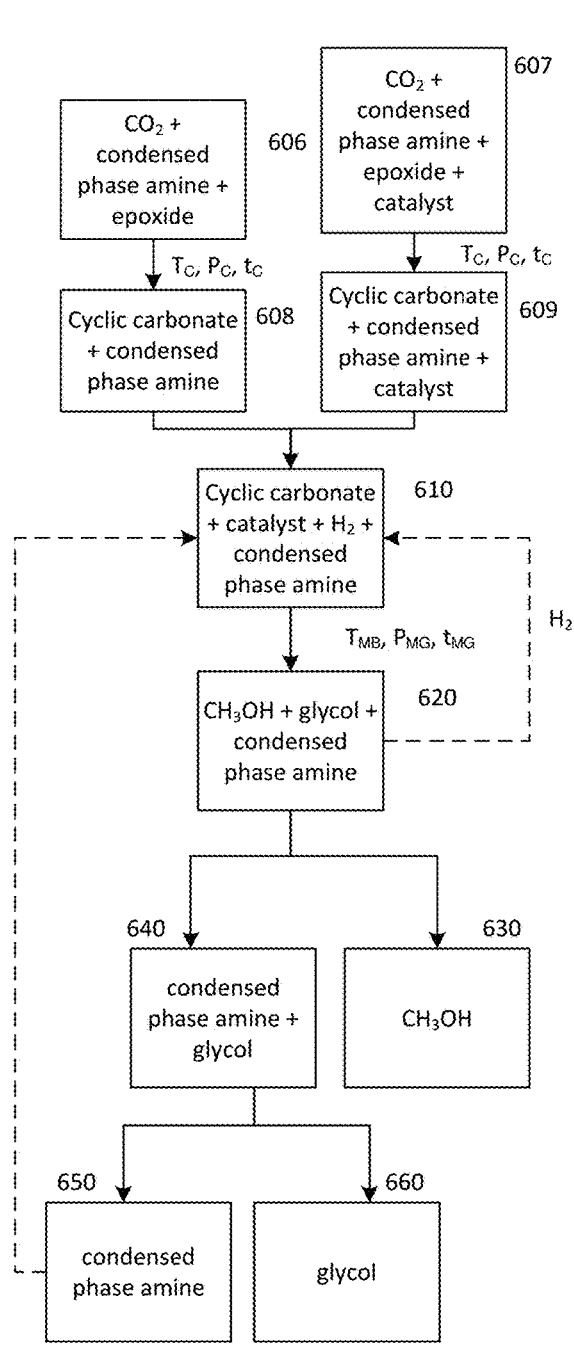
FIG. 6 is a flow diagram of another exemplary embodiment of a process for converting CO$_2$ to methanol and a glycol.

In some embodiments, the process of converting the captured CO$_2$ to methanol and glycol is a two-step process, comprising (i) cycloaddition of the CO$_2$ to the epoxide to form a cyclic carbonate-containing mixture comprising a cyclic carbonate and the condensed phase amine and (ii) subsequent hydrogenation of the cyclic carbonate-containing mixture in the presence of a hydrogenation catalyst and H$_2$ to form methanol and glycol. Embodiments of the disclosed process do not require added water. Instead, water is produced and consumed in situ. FIG. 6 illustrates one embodiment of a two-step process. CO$_2$ is combined with an epoxide and a condensed phase comprising an amine (606). The combined components are subjected to an effective temperature $T_C$ and initial pressure $P_C$ for a sufficient time $t_C$ to form a cyclic carbonate-containing mixture comprising a cyclic carbonate and the condensed phase comprising the amine (608). The cyclic carbonate-containing mixture is combined with a hydrogenation catalyst and H$_2$ (610) and subjected to an effective temperature $T_{MG}$ and initial pressure $P_{MG}$ for a sufficient time $t_{MG}$ to form a solution comprising CH$_3$OH, glycol, and the condensed phase comprising the amine (620), where $T_{MG}$, $P_{MG}$, and $t_{MG}$ are as previously described. In an alternative embodiment, CO$_2$ is combined with an epoxide, a condensed phase comprising an amine, and a hydrogenation catalyst (607). The combined components are subjected to an effective temperature $T_C$ and initial pressure $P_C$ for a sufficient time $t_C$ to form a cyclic carbonate-containing mixture comprising a cyclic carbonate and the amine (609). The cyclic carbonate-containing mixture, along with the hydrogenation catalyst, is combined with $H_2$ (610) and subjected to an effective temperature $T_{MG}$ and initial pressure $P_{MG}$ for a sufficient time $t_{MG}$ to form a solution comprising $CH_3OH$, glycol, and the condensed phase comprising the amine (620), where $T_{MG}$, $P_{MG}$, and $t_{MG}$ are as previously described. In any of the foregoing embodiments, a separation then is performed to provide $CH_3OH$ (630) and a solution comprising the glycol and the condensed phase comprising the amine (640). The separation may be performed by any suitable method. In some embodiments, a flash separation or distillation may be performed by any suitable method as set forth above. The glycol and the condensed phase comprising the amine are then separated (e.g., by distillation) to provide the condensed phase comprising the amine (650) and glycol (660). The condensed phase comprising the amine (650) is optionally recycled and reused. In some examples, the $CH_3OH$ and glycol may be removed together from the amine, and the $CH_3OH$ and glycol are then separated, e.g., by distillation (not shown).

In any of the foregoing embodiments, the temperature $T_C$ may be within a range of from 25° C. to 180° C., such as from 100-180° C., 100-170° C., 120-160° C., or 130-150° C. In any of the foregoing embodiments, the initial pressure $P_C$ may be within a range of from 0.1 MPa to 2 MPa, such as 0.1-1 MPa. In any of the foregoing embodiments, the time $t_C$ may be within a range of from 3 seconds to 36 hours, such as from 15 seconds to 36 hours, 30 seconds to 36 hours, 1 minute to 36 hours, 5 minutes to 36 hours, 10 minutes to 36 hours, 30 minutes to 36 hours, 1-36 hours, 3-36, 6-24 hours, 12-18 hours, 3 seconds to 3 hours, 3 seconds to 1 hour, 5 seconds to 1 hour, 10 seconds to 30 minutes, or 15 seconds to 15 minutes. In a continuous process, the time to may be on the order of a few seconds to several minutes, whereas the time to may be on the order of several hours in a batch process. In certain embodiments where $T_C$>60° C., a period of time is allowed for $CO_2$ capture before increasing the temperature to $T_C$. The period of time for initial $CO_2$ capture may range from a few seconds to several hours, with longer times being used in batch processes.

Figure 7:
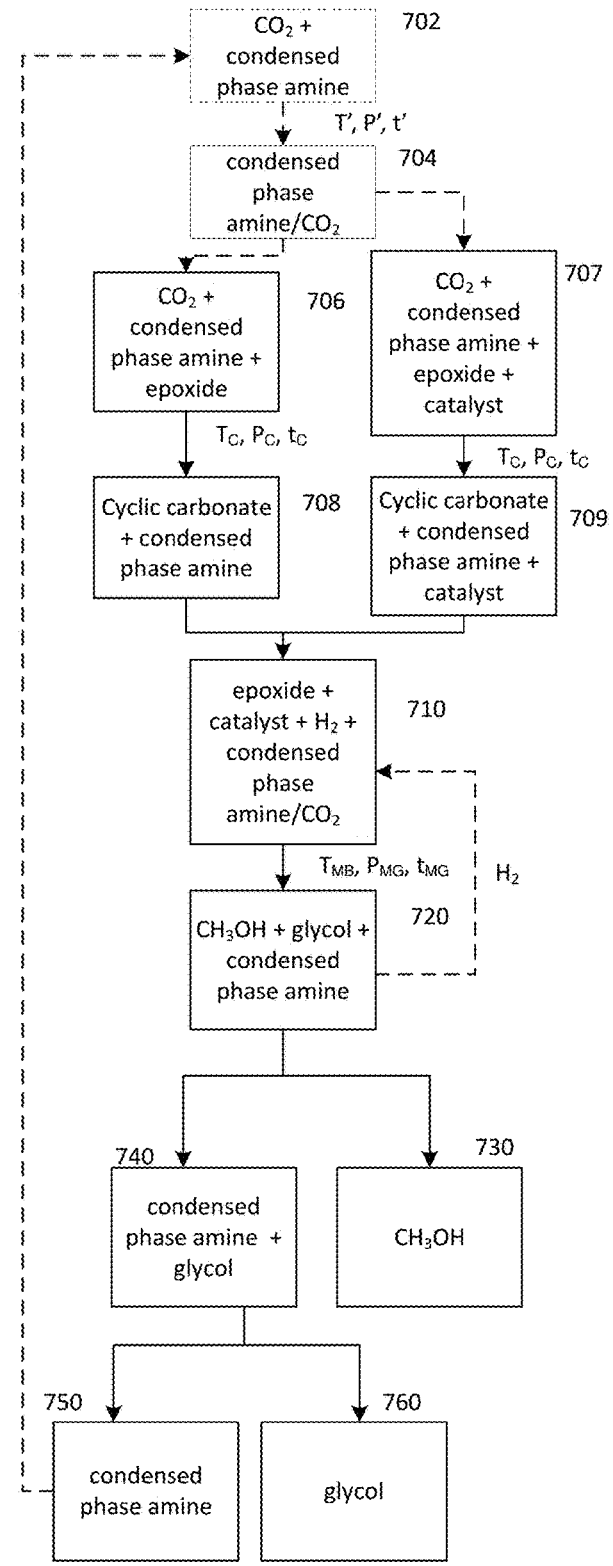
FIG. 7 is a flow diagram of another exemplary embodiment of a process for converting CO$_2$ to methanol and a glycol.

In an independent embodiment, the $CO_2$ is present in the condensed phase comprising the amine prior to combining the condensed phase with the epoxide, hydrogenation catalyst, and hydrogen. In such embodiments, the condensed phase is a solution comprising the amine, $CO_2$, and optionally a solvent. As shown in FIG. 7, the process optionally includes combining $CO_2$ with a condensed phase comprising the amine (702) under effective conditions to form a condensed phase comprising the amine, the $CO_2$, and optionally a solvent (704). The effective conditions include a temperature T', an initial pressure P', and time t' sufficient for the condensed phase amine to capture $CO_2$, thereby providing a condensed phase comprising the amine and captured $CO_2$. The temperature T', initial pressure P', and time t' are as previously described. In other embodiments, the process may commence with a condensed phase comprising the amine and captured $CO_2$ (704). The condensed phase comprising the amine and $CO_2$ is combined with the epoxide (706). The combined components are subjected to an effective temperature $T_C$ and initial pressure $P_C$ for a sufficient time $t_C$ to form a cyclic carbonate-containing mixture comprising a cyclic carbonate and the condensed phase comprising the amine (708). $T_C$, $P_C$, and $t_C$ are as previously described. The cyclic carbonate-containing mixture is combined with a hydrogenation catalyst and $H_2$ (710) and subjected to an effective temperature $T_{MG}$ and initial pressure $P_{MG}$ for a sufficient time $t_{MG}$ to form a solution comprising $CH_3OH$, glycol, and the condensed phase comprising the amine (720), where $T_{MG}$, $P_{MG}$, and $t_{MG}$ are as previously described. In an alternative embodiment, $CO_2$ is combined with an epoxide, a condensed phase comprising an amine, and a hydrogenation catalyst (707). The combined components are subjected to an effective temperature $T_C$ and initial pressure $P_C$ for a sufficient time $t_C$ to form a cyclic carbonate-containing mixture comprising a cyclic carbonate and the amine (709). The cyclic carbonate-containing mixture, along with the hydrogenation catalyst, is combined with $H_2$ (710) and subjected to an effective temperature $T_{MG}$ and initial pressure $P_{MG}$ for a sufficient time $t_{MG}$ to form a solution comprising $CH_3OH$, glycol, and the condensed phase comprising the amine (720), where $T_{MG}$, $P_{MG}$, and $t_{MG}$ are as previously described. In any of the foregoing embodiments, a separation then is performed to $CH_3OH$ (730) and a solution comprising the glycol and the condensed phase comprising the amine (740). The separation may be performed by any suitable method. In some embodiments, a flash separation or distillation may be performed by any suitable method as set forth above. The glycol and the condensed phase comprising the amine are then separated (e.g., by distillation) to provide the condensed phase comprising the amine (750) and glycol (760). The condensed phase comprising the amine (750) is optionally recycled and reused. In some examples, the $CH_3OH$ and glycol may be removed together from the amine, and the $CH_3OH$ and glycol are then separated, e.g., by distillation (not shown).

Figure 8A:
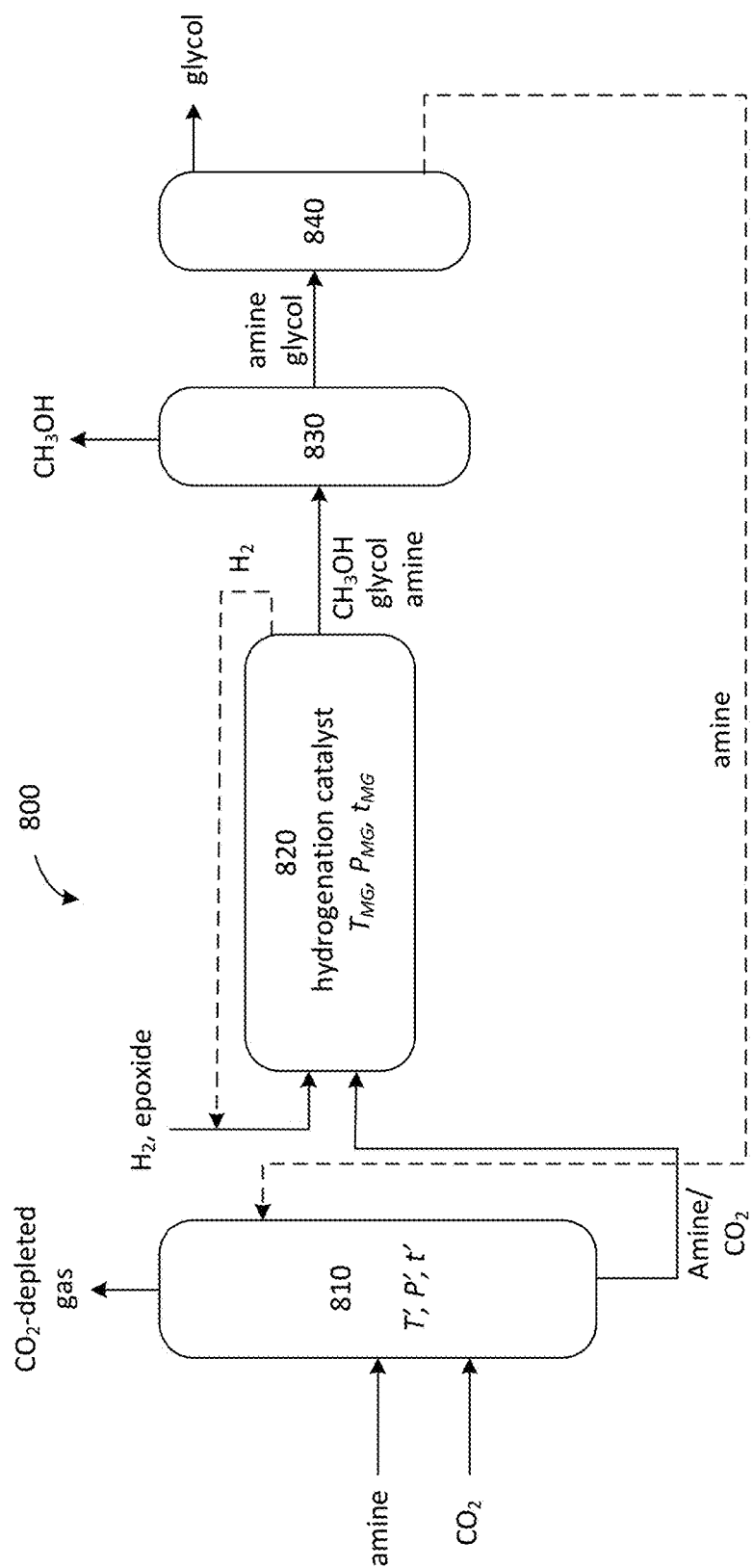
FIGS. 8A and 8B are simplified schematic diagrams of an exemplary apparatus for performing the process of FIG. 5.
Figure 8B:
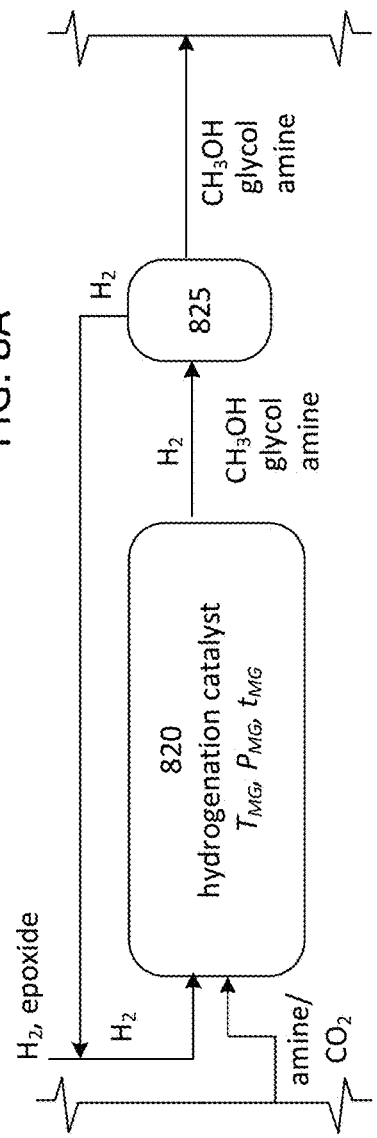

FIG. 8A is a schematic diagram of one embodiment of an apparatus 800 for performing the method of FIG. 5. A condensed phase comprising an amine and a gas flow comprising $CO_2$ are flowed into a $CO_2$ absorber 810. The condensed phase and the $CO_2$ are subjected to a temperature T', an initial pressure P', and time t' sufficient for the amine to capture the $CO_2$ to form a condensed phase solution comprising the amine and $CO_2$. A $CO_2$-depleted gas is exhausted from the $CO_2$ absorber 810. The condensed phase solution flows into a hydrogenation reactor 820 where it is combined with $H_2$, an epoxide, and a hydrogenation catalyst disposed within the hydrogenation reactor 820. In any of the foregoing embodiments, the hydrogenation catalyst may be disposed in a fixed bed or a fluidized bed within the hydrogenation reactor 820. If the bed is a fluidized bed, the $H_2$ flow may be used for the fluidization. The combined components are subjected to an effective temperature $T_{MG}$ and initial pressure $P_{MG}$ for a sufficient time $t_{MG}$ to form a condensed phase solution comprising $CH_3OH$, glycol, and the amine. $T_{MG}$, $P_{MG}$, and $t_{MG}$ are as previously described. In any of the foregoing embodiments, the condensed phase solution, the hydrogen, or both may be pre-heated to a temperature ranging from greater than ambient to $T_{MG}$ before entering the hydrogenation reactor. In some embodiments, the $H_2$ flowing into the hydrogenation reactor 820 is in stoichiometric excess relative to the $CO_2$ in the condensed phase, and excess $H_2$ exiting the hydrogenation reactor optionally is recycled back into the hydrogenation reactor. In certain embodiments, e.g., as shown in FIG. 8B, the excess $H_2$ and the condensed phase solution comprising the $CH_3OH$, glycol, and the amine exiting the hydrogenation reactor 820 are flowed into a separator 825 where the $H_2$ is separated from the solution and subsequently recycled to the hydrogenation reactor 820. The $H_2$ and the condensed phase solution may be cooled, e.g., to 30-50° C. before entering the separator 825. In some embodiments, the separator 825 is a flash drum, such as a low-temperature flash drum operating at a temperature of 20-50° C., such as 30-50° C., and a pressure of 1-5 MPa, such as 2-3 MPa. The condensed phase solution comprising the $CH_3OH$, glycol, and the amine exiting the hydrogenation reactor 820 (or separator 825) is flowed into a separator 830 where the glycol and condensed phase amine are separated from the $CH_3OH$. In some embodiments, the separator 830 is a flash drum or a distillation column. In certain embodiments, the separator 830 is a flash drum operating at a temperature within a range of from 100-150° C., such as 120-140° C., and a pressure of 0.1-1 MPa, such as 0.1-0.5 MPa. The glycol and condensed phase amine are flowed into a distillation column 840 where the glycol and the condensed phase amine are separated. The condensed phase amine optionally is recycled back to the $CO_2$ absorber 810.

In an alternative embodiment, the apparatus 800 of FIGS. 8A and 8B may be used to perform the method of FIG. 7. In such an embodiment, the condensed phase solution flows into a hydrogenation reactor 820 where it is combined with the epoxide and the hydrogenation catalyst disposed within the hydrogenation reactor 820. The combined components are subjected to an effective temperature $T_C$ and initial pressure $P_C$ for a sufficient time $t_C$ to form a cyclic carbonate-containing mixture comprising a cyclic carbonate and the amine. $T_C$, $P_C$, and $t_C$ are as previously described. $H_2$ is then flowed into the hydrogenation reactor 820, and the combined components are subjected to an effective temperature $T_{MG}$ and initial pressure $P_{MG}$ for a sufficient time $t_{MG}$ to form a condensed phase solution comprising $CH_3OH$, glycol, and the amine. $T_{MG}$, $P_{MG}$, and $t_{MG}$ are as previously described. The remainder of the process proceeds as described above.

Figure 9A:
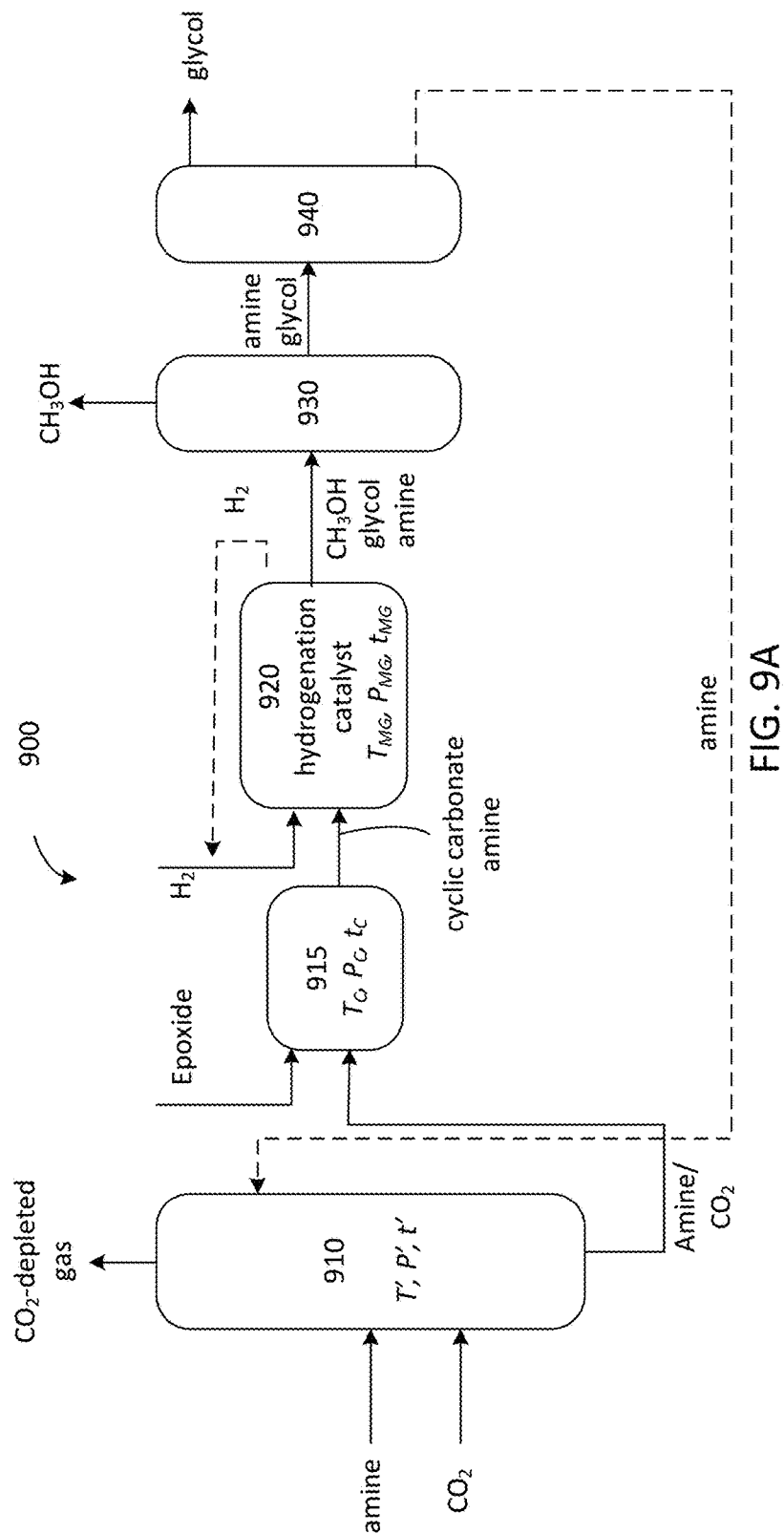
FIGS. 9A and 9B are simplified schematic diagrams of an exemplary apparatus for performing the process of FIG. 7.
Figure 9B:
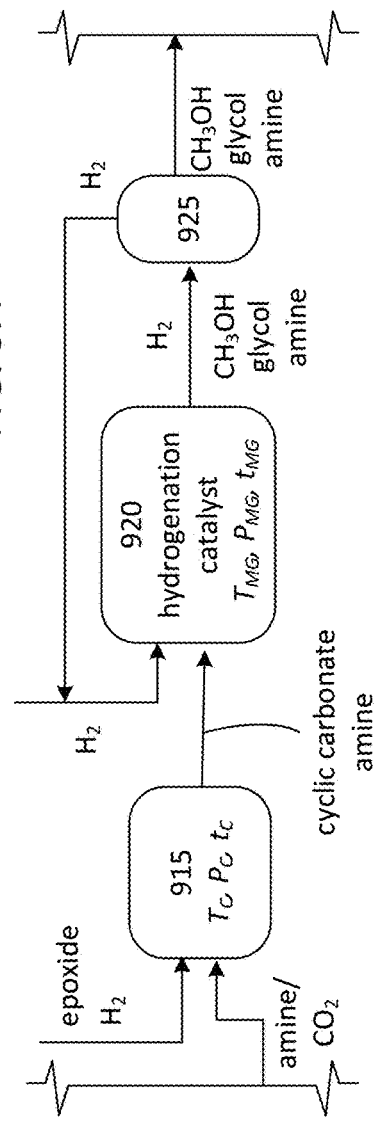

FIG. 9A is a schematic diagram of one embodiment of an apparatus 900 for performing the method of FIG. 7. A condensed phase amine and a gas flow comprising $CO_2$ are flowed into a $CO_2$ absorber 910. The condensed phase amine and $CO_2$ are subjected to a temperature T', an initial pressure P', and time t' sufficient for the condensed phase amine to capture the $CO_2$ to form a condensed phase solution comprising the amine and $CO_2$. A $CO_2$-depleted gas is exhausted from the $CO_2$ absorber 910. The condensed phase solution flows into a cycloaddition reactor 915 where it is combined with an epoxide. The combined components are subjected to an effective temperature $T_C$ and initial pressure $P_C$ for a sufficient time $t_C$ to form a cyclic carbonate-containing mixture comprising a cyclic carbonate and the amine. $T_C$, $P_C$, and $t_C$ are as previously described. The cyclic carbonate-containing mixture is flowed into the condensed phase hydrogenation reactor 920 where it is combined with $H_2$ and a hydrogenation catalyst disposed within the hydrogenation reactor 920. In any of the foregoing embodiments, the hydrogenation catalyst may be disposed in a fixed bed or a fluidized bed within the hydrogenation reactor 920. If the bed is a fluidized bed, the $H_2$ flow may be used for the fluidization. The combined components are subjected to an effective temperature $T_{MG}$ and initial pressure $P_{MG}$ for a sufficient time $t_{MG}$ to form a condensed phase solution comprising $CH_3OH$, glycol, and the amine. In any of the foregoing embodiments, the cyclic carbonate-containing mixture, the hydrogen, or both may be pre-heated to a temperature ranging from greater than ambient to $T_{MG}$ before entering the hydrogenation reactor. In some embodiments, the $H_2$ flowing into the hydrogenation reactor 920 is in stoichiometric excess relative to the $CO_2$ in the condensed phase, and excess $H_2$ exiting the hydrogenation reactor optionally is recycled back into the hydrogenation reactor. In certain embodiments, e.g., as shown in FIG. 9B, the excess $H_2$ and the condensed phase solution comprising the $CH_3OH$, glycol, and amine exiting the hydrogenation reactor 920 are flowed into a separator 925 where the $H_2$ is separated from the solution and subsequently recycled to the hydrogenation reactor 920. The $H_2$ and the solution may be cooled, e.g., to 30-50° C. before entering the separator 925. In some embodiments, the separator 925 is a flash drum, such as a low-temperature flash drum operating at a temperature of 20-50° C., such as 30-50° C., and a pressure of 1-5 MPa, such as 2-3 MPa. The condensed phase solution comprising the $CH_3OH$, glycol, and amine exiting the hydrogenation reactor 920 (or separator 925) is flowed into a separator 930 where glycol and the condensed phase amine are separated from the $CH_3OH$. In some embodiments, the separator 930 is a flash drum. In certain embodiments, the separator 930 is a flash drum operating at a temperature within a range of from 100-150° C., such as 120-140° C., and a pressure of 0.1-1 MPa, such as 0.1-0.5 MPa. The glycol and condensed phase amine are flowed into a distillation column 940 where the glycol and the condensed phase amine are separated. The condensed phase amine optionally is recycled back to the $CO_2$ absorber 910.

In any of the foregoing embodiments, the process may be a batch process or a continuous process. Some embodiments of the apparatus shown in FIGS. 8A-B and 9A-B may be suitable for a continuous process. In a continuous process, the hydrogenation catalyst may be disposed in a fixed bed in the hydrogenation reactor 820/920, and the $H_2$ and the condensed phase solution comprising the amine and $CO_2$ flow through or across the fixed bed. Alternatively, the hydrogenation catalyst may be disposed in a fluidized bed in the hydrogenation reactor 820/920, where the bed is fluidized by the $H_2$ flow and/or the condensed phase solution, and the $H_2$ and the condensed phase solution comprising the amine and $CO_2$ flow through the fluidized bed. In some embodiments, the condensed phase solution is flowed through the hydrogenation reactor at a space velocity of from greater than 0 to 50,000 $hr^{-1}$, such as from 1-50,000, 100-50,000, 500-40,000, 500-30,000, or 1,000-25,000 $hr^{-1}$. In some embodiments, a lower space velocity provides an increased conversion of $CO_2$ to methanol and glycol. In the embodiments of FIGS. 9A-B, the condensed phase solution comprising the $CO_2$, amine, and epoxide may be flowed through the cycloaddition reactor 915 at a space velocity of from greater than 0 to 50,000 $hr^{-1}$, such as from 1-50,000, 100-50,000, 500-40,000, 500-30,000, or 1,000-25,000 $hr^{-1}$. In some embodiments, the space velocities through the cycloaddition reactor and hydrogenation reactor are substantially the same.

In an exemplary embodiment, a one-step process for converting $CO_2$ to methanol and propylene glycol comprises combining propylene oxide, a Ru-based hydrogenation catalyst, $CO_2$ and $H_2$ (in a ratio of 2:7) with a condensed phase comprising PEI and THF. The combined components are heated to 140° C. at an initial pressure of 7 MPa for 24 h.

In another exemplary embodiment, a two-step process for converting $CO_2$ to methanol and propylene glycol comprises combining propylene oxide and $CO_2$ with a condensed phase comprising PEI and THF at an initial pressure of 2 MPa, and heating to 140° C. for 16-24 h to form propylene carbonate. Subsequently, the reactor is cooled to 0° C. and pressure is released. A Ru-based hydrogen catalyst and $H_2$ ($CO_2$:$H_2$ molar ratio 1:3) are added to an initial pressure of 6 MPa, and the components are heated to 140° C. for 16 h to form methanol and propylene glycol.

In yet another exemplary embodiment, a two-step process for converting $CO_2$ to methanol and propylene glycol comprises combining a Ru-based hydrogenation catalyst, propylene oxide, and $CO_2$ with a condensed phase comprising PEI and THF at an initial pressure of 2 MPa, and heating to 140° C. for 16-24 h to form propylene carbonate. Subsequently, the reactor is cooled to 0° C. and pressure is released. $H_2$ ($CO_2$:$H_2$ molar ratio 1:3) is added to an initial pressure of 6 MPa, and the components are heated to 140° C. for 16 h to form methanol and propylene glycol.

In any of the foregoing exemplary embodiments, the Ru-based hydrogenation catalyst may be a Ru-pincer catalyst. In certain embodiments, the catalyst is

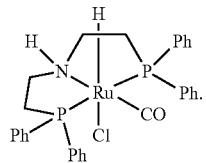

VI. Examples

General:

All manipulations were performed using a $N_2$-atmosphere glovebox or standard Schlenk techniques. The catalysts 1, 2 and 3 were obtained from Strem chemicals. Standard solvents were purified by passing through a neutral alumina column (Innovative Technology, Inc., PureSolv™ solvent purification system). All deuterated solvents were purchased from Cambridge Isotope Laboratories, Inc. Anhydrous propylene oxide was purchased from Sigma-Aldrich. All other materials were purchased from commercial suppliers and used without further purification unless otherwise mentioned. Monoethanolamine (MEA) and diethylethanolamine (DEEA) were distilled over $CaH_2$ and stored in the glovebox. 4-Dimethylaminopyridine (DMAP) and polyethyleneimine $M_n$ 600 ($PEI_{600}$) were dried under vacuum overnight and stored in the glovebox. $^1H$ and $^{13}C$ NMR experiments were recorded on a 500 MHz Varian NMR spectrometer. The NMR chemical shifts were assigned relative to the internal standard, 1,3,5-trimethoxybenzene (TMB). The headspace gas was analyzed using an Agilent Technologies 6850 GC System equipped with a Supelco 10 ft×⅛ inch carbosieve column equipped with a thermal conductivity detector (TCD). MAS-NMR experiments were performed on an Agilent-Varian VNMRS NMR spectrometer equipped with an 11.7 T magnet, operating at 125.7747 MHz for the $^{13}C$ channel and 500.1822 MHz for $^1H$ channel, and using a 5 mm homebuilt MAS double-resonance HX probe with a custom Pd-coated coil for increased sample magnetic homogeneity. The rotor was heated to various set temperatures and both $^{13}C$ and $^1H$ spectra were collected before further temperature elevation. All rotors were Varian/Agilent-style cavern rotors (Revolution NMR LLC), modified for high pressure samples as described previously (Walter et al., *J Phys Chem C* 2018, 122(15):8209-8215). A premixed solution containing propylene oxide (240 mg), $PEI_{600}$ (60 mg), catalyst 3 (2.4 mg) and THF-$d_8$ (1 mL) was transferred to a MAS NMR rotor in a $N_2$-atmosphere glovebox. The rotor was charged with a 15 bar $CO_2$ and 60 bar $H_2$ at room temperature (total initial pressure=60 bar) and heated to 140° C.

Example 1

Figure 10:
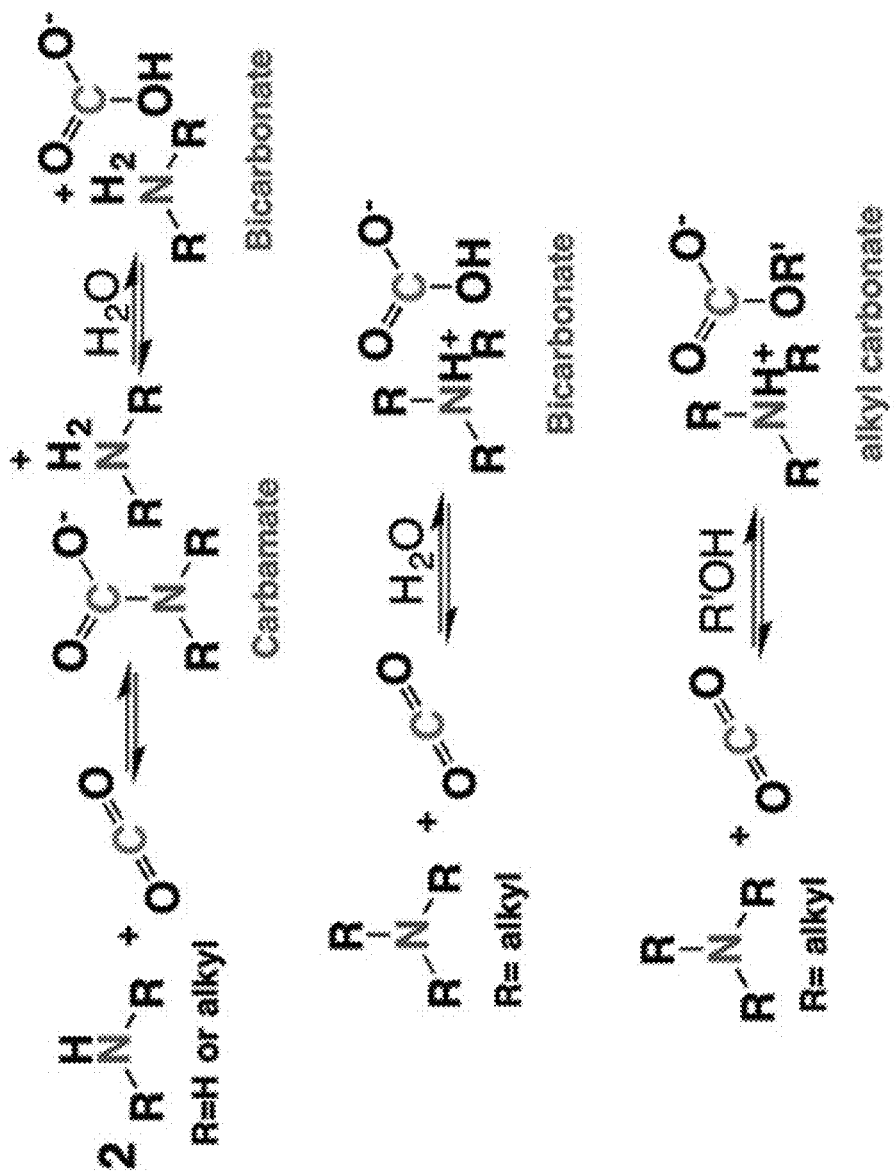
FIG. 10 shows reaction schemes for CO$_2$ capture using different amines.

Conversion of $CO_2$ to Methanol $CO_2$ can be captured from air or concentrated sources by amine, amine/$H_2O$, or an amine/alcohol mixture to form carbamate, bicarbonate, or carbonate, respectively (FIG. 10). The $CO_2$ activated in this fashion can be utilized to produce $CO_2$-derived products, such as methanol.

As a catalyst, 300 mg of commercial Cu/ZnO/$Al_2O_3$ catalyst from Synetix was activated under $H_2$ atmosphere (48 bar, 4.8 MPa) at 125° C. in a stainless-steel reactor (8 mL). After 4 h, the remaining $H_2$ pressure from the reactor was released and backfilled with $H_2$ at 125° C. and cooled to room temperature. The commercial black Cu/ZnO/$Al_2O_3$ catalyst's color changed to purple-black powder after the activation. The catalyst contained 55.7 wt. % Cu, 26.8 wt. % Zn, and 5.0 wt. % Al according to inductively coupled plasma optical emission spectroscopy (ICP-OES) analysis.

The pre-activated catalyst was transferred to a 300 mL Parr reactor and a given amount of amine and alcohol were added to the reactor vessel and the reactor was sealed in a nitrogen glovebox. The reactor was first pressurized with 20 bar (2 MPa) $CO_2$ and then additional 40 bar (4 MPa) of $H_2$ was introduced (total pressure=60 bar, 6 MPa). Then, the reactor was heated to 170° C. After 16 h, the reactor was cooled to room temperature and then to −78° C., the excess pressure was released slowly. 100 mg of 1,3,5-trimethoxybenzene was added as an internal standard to the reaction mixture (if necessary, DMSO or water was added to get a homogeneous solution) and a small aliquot of the sample was analyzed by $^1H$ and $^{13}C$ NMR in $CDCl_3$ or $D_2O$. The results are shown in Table 1.

TABLE 1

| Entry | Promoter | HCOO⁻ (%) | HCOOEt (%) | $CH_3OH$ (%) |
|---|---|---|---|---|
| 1 | $NEt_3$ | Trace | — | — |
| 2 | EtOH | — | — | — |
| 3 | $NEt_3$:EtOH 1:1 | Trace | Trace | 2% |
| 4 | $NEt_3$:EtOH 10:1 | — | — | — |
| 5 | $NEt_3$:EtOH 1:10 | 3% | Trace | 100% |
| 6[a] | $NEt_3$:EtOH 1:10 | 3% | 1% | 76% |
| 7[b] | $NEt_3$:EtOH 1:10 | — | 1% | 28% |
| 8[c] | $NEt_3$:EtOH 1:10 | 4% | 4% | 19% |
| 9 | $NEt_3$:EtOH 1:5 | Trace | Trace | 7% |
| 10 | TMEA:EtOH 1:10 | — | 1% | 18% |
| 11 | DEEA:EtOH | 0.5% | Trace | 21% |

EtOH = ethanol; $NEt_3$ = triethylamine; TMEA = tetramethylethylenediamine, DEEA = diethylethanolamine.
Standard reaction conditions: 300 mg Cu/ZnO/$Al_2O_3$ catalyst, $CO_2$/$H_2$ = 60 bar (6 MPa, 1:2), EtOH (200 mmol), amine (20 mmol), T = 170° C., t = 16 h.
HCOO⁻, HCOOEt, and $CH_3OH$ yields are based on $^1H$ NMR.
Yields are calculated with respect to the amine.
[a]40 h,
[b]150° C.,
[c]120° C.

An initial screening showed that 1° and 2° amines (e.g., ethylenediamine and dibutylamine) were hydrogenated to formamides, but were unable to continue to $CH_3OH$. Tertiary amines, e.g., $NEt_3$, were found to be nonreactive, as were alcohols. However, the combination of 3° and alcohol produced $CH_3OH$ (entries 1-3, Table 1). These results suggested that the neutral $CO_2$ might not be the active species. The tertiary alkanolamines, N,N,N'N'-tetrakis(2-hydroxyethyl)ethylenediamine (THEED) and triethanolamine (TEA) decomposed at a high temperature. Diethylethanolamine (DEEA), however, produced 6.5 mmol of $CH_3OH$ (4% conversion based on amine). Changing the ratio of amine to alcohol influenced the conversion to $CH_3OH$; when the ratio of amine to alcohol was 10:1, the conversion to $CH_3OH$ with respect to amine was poor, whereas a ratio of 1:10 enabled a 100% conversion to $CH_3OH$ with respect to amine (entries 4 and 5, Table 1). A $CH_3OH$ synthesis activity as high as 4166 mmol $kg^{-1}$ $cat^{-1}$ $h^{-1}$ was obtained at 170° C. with a $CH_3OH$ yield of ~10% with respect to $CO_2$. An excess of $NEt_3$ could passivate the catalyst surface, limiting the reaction. It is likely that polarity has a strong influence on the reactivity as we have shown the formation of alkylcarbonates to be highly sensitive with respect to polarity. The relatively lower polarity of $NEt_3$ would disfavor the formation of the highly polar alkylcarbonate, whereas the polarity of excess alcohol would be enough to favor alkylcarbonate formation. Further EtOH could solvate polar transition states and charged intermediates common to $CO_2$ hydrogenation whereas $NEt_3$ would not. Excess alcohol would also promote the thermal esterification to produce formate ester. Gas chromatographic analysis of the gas mixtures only showed trace amounts of $CH_4$ and CO in addition to excess $H_2$ and $CO_2$.

The necessity for the combination of non-nucleophilic bases and alcohols suggests that $CH_3OH$ production proceeds via formate and formate ester routes. The presence of amine and alcohol promotes the formation of alkylcarbonate, ammonium formate and alkyl formate ester intermediates. Under optimal conditions, the amount of $CH_3OH$ produced never surpassed the amount of amine used regardless of time, which suggested an established equilibrium (entry 6, Table 1). Even at lower temperatures 150° C. and 120° C., moderate $CH_3OH$ yields were obtained (entries 7 and 8), suggesting that the reaction does not necessarily need to proceed at 170° C. Tetramethylethylenediamine (TMEA) and DEEA formed 18% and 21% $CH_3OH$, respectively in the presence of excess ethanol (entries 10 and 11). It was clear that excess alcohol does not improve the amount of $CH_3OH$ formed in the case of DEEA as it decomposes under these conditions.

The effect of basicity on the alkylcarbonate formation capacity of amines and alcohols on the $CH_3OH$ formation was then studied. The alkyl carbonate formation in Table 2 was studied under high pressure since some alkylcarbonates are not stable under atmospheric conditions. Under an inert atmosphere, 0.0012 mol of amine was dissolved in 3.0 mL of methanol. The solution was syringed into the stainless-steel IR cell or into a PEEK high pressure NMR cell and charged with 1 MPa $CO_2$ at room temperature. The NMR cells were agitated by vortex until equilibrium has been reached.

Figures 11, 12:
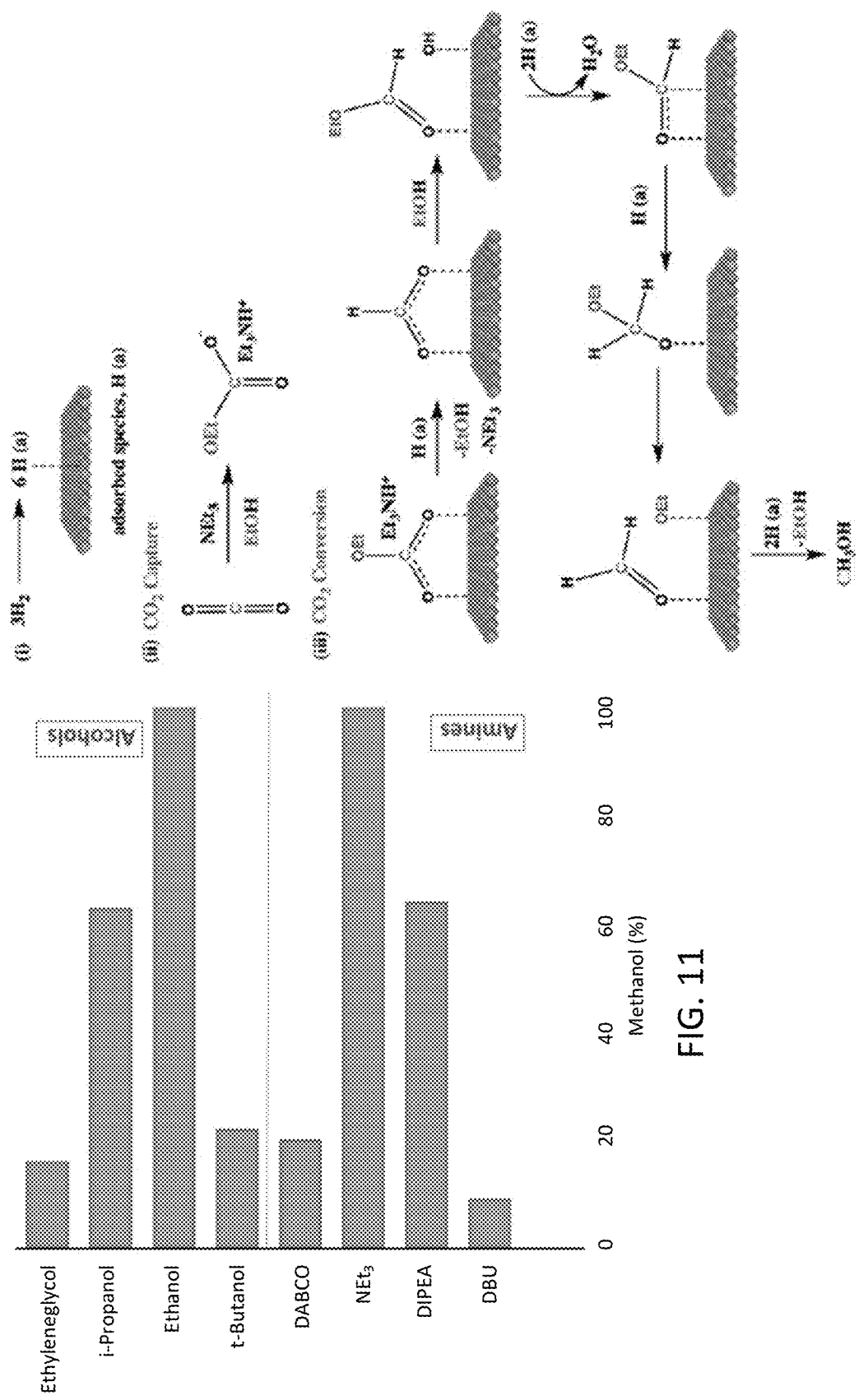
FIG. 11 is a bar graph showing methanol yields from CO$_2$ using various alcohols and amines.
FIG. 12 illustrates a potential reaction mechanism for conversion of CO$_2$ to methanol in the presence of triethylamine and ethanol.

From Table 2, it is clear that the strong bases provide high methyl carbonate yields, but low $CH_3OH$ yields (FIG. 11). Meanwhile, less basic amines gave moderate methyl carbonate yields but high $CH_3OH$ yields. $NEt_3$ showed the highest $CH_3OH$ yield, suggesting that having a conjugate acid of the amine that is weaker than the corresponding alkylcarbamic or alkylcarbonic acids in $H_2O$ is optimal under these conditions. Since aromatic ring hydrogenation was observed in the presence of the $Cu/ZnO/Al_2O_3$ catalyst, DMAP and pyridine were not selected for further study.

TABLE 2

| Entry | Amine | Conjugate Acid $pK_a$ | Methyl carbonate (%) | IR (CO) $cm^{-1}$ | $^{13}C$ NMR (ppm) $I^a$ | $II^b$ |
|---|---|---|---|---|---|---|
| 1 | DBU | 12 | 98 | 1642 | 52.2 | 159.8 |
| 2 | DIPEA | 11.4 | 92 | 1647 | 51.1 | 158.8 |
| 3 | $NEt_3$ | 10.6 | 75 | 1654 | 52.3 | 160.1 |
| 4 | DMAP | 9.9 | 64 | 1651 | 52.4 | 160.5 |
| 5 | DABCO | 8.8 | 64 | 1650 | 49.1 | 160.0 |
| 6 | Pyridine | 5.5 | No reaction | | | |

Standard reaction conditions: alkylcarbonate formation from $CO_2$ capture - alkylcarbonate yield calculated with respect to amine by $^{13}C$ NMR of 2 M amine in $CH_3OH$ under 10 bar (1 MPa) $CO_2$ at room temperature.
[a] NMR resonance of methyl carbon in $CH_3OCOO^-$ species.
[b] NMR resonance of carbonate carbon in $CH_3OCOO^-$ species.
DBU = 1,8-diazabicyclo[5.4.0]undec-7-ene,
DIPEA = N,N-diisopropylethylamine,
DMAP = 4-dimethylaminopyridine,
DABCO = 1,4-diazabicyclo[2.2.2]octane.

Similarly, the choice of alcohol was investigated under pressure (Table 3). Under an inert atmosphere, 0.0012 mol of $NEt_3$ was dissolved in 3.0 mL of alcohol. The solution was syringed into a PEEK high pressure NMR cell and charged with 1 MPa $CO_2$ at room temperature. Under an inert atmosphere, 0.0012 mol of $NEt_3$ and 0.0012 mol of phenol were dissolved in 3.0 mL of THF. The solution was syringed into a PEEK high pressure NMR cell and charged with 1 MPa $CO_2$ at room temperature.

The presence of $CH_3OH$ or EtOH did not show significant difference in the alkylcarbonate yield, which was attributed to similar $pK_a$ values of the alcohols. However, the alkyl chain length and sterics significantly reduced the alkylcarbonate conversion and $CH_3OH$ yields (FIG. 11). This result was consistent with previous observations that secondary alcohols do not form as much alkylcarbonate as linear alcohols due to steric crowding. Similarly phenol likely is not electrophilic enough to attack $CO_2$ and does not carboxylate under the evaluated conditions. The results obtained in Tables 2 and 3 and FIG. 11 suggested that the tertiary amines and short linear alcohols were the best combination for high $CH_3OH$ yields, consistent with the conditions that favor alkylcarbonate formation.

TABLE 3

| Entry | Alcohol (%) | pKa | Alkyl carbonate (%) |
|---|---|---|---|
| 1 | $CH_3OH$ | 16 | 75 |
| 2 | EtOH | 15.9 | 75 |
| 3 | i-Propanol | 16.5 | 25 |
| 4 | Ethyleneglycol[a] | 14.2 | 35 |
| 5 | t-Butanol | 17 | No reaction |
| 6 | Phenol[b] | 10 | No reaction |

Standard reaction conditions: alkylcarbonate formation from $CO_2$ capture - alkylcarbonate yield calculated with respect to amine by $^{13}C$ NMR of 2M $NEt_3$ in alcohol under 10 bar (1 MPa) $CO_2$ at room temperature.
[a] Only one OH group is carbonated.
[b] The reaction was performed in THF.

While a direct correlation between the alkylcarbonate formed and $CH_3OH$ formation was observed (Tables 2 and 3), it is expected that there is a small amount of alkylcarbonate present at 170° C. under 2.5 MPa $CO_2$. A plausible reaction mechanism via the coordination of anionic ethyl carbonate to the catalyst surface, by which the reaction proceeds via formate and ethyl formate intermediates is proposed (FIG. 12).

Figure 13:
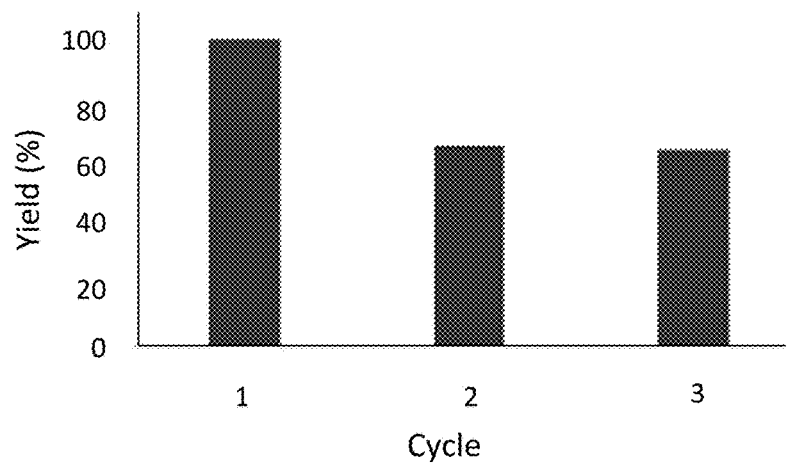
FIG. 13 is a bar graph showing catalytic activity of a recycled Cu/ZnO/Al$_2$O$_3$ catalyst over three cycles.

Catalyst recycling was studied under 1:2 $CO_2:H_2$ pressure. In the second run, some drop in catalytic activity was observed (FIG. 13). However, the activity remained the same in the third run. The decrease in the catalytic activity was probably due to the catalyst sintering, which was confirmed by powder X-ray diffraction (XRD) performed after the third run. X-ray diffraction (XRD) patterns were obtained using a Rigaku MiniFlex II powder x-ray diffractometer with a Cu-kα x-ray source operated at 30 kV and 15 mA with an amorphous glass sample holder. Prior to measurement, the fresh sample was ground and reduced at 125° C. for 4 h under 48 bar $H_2$ atmosphere. The spent sample was collected and used as recovered. XRD patterns were collected from 10 to 80° 2θ at a step size of 0.02° 2θ/step. Peaks were analyzed and fit using the MDI Jade 9 software. $Cu^0$ crystallite size was calculated using the Scherer equation based on the 43.5° 2θ peak. Cu dispersion was calculated from the $Cu^0$ particle size assuming hemispherical geometry using the formula D=100/d where D represents the fractional dispersion and d is the $Cu^0$ particle size (in nm). The Cu particle size increased from 21 nm (freshly reduced) to 40 nm (spent). Similar sintering of the catalyst in a batch reactor was observed previously in the presence of $H_2O$, the by-product. XRD analysis also showed the presence of $ZnCO_3$, which could have formed from an excess $CO_2$ concentration under pressurized conditions. Thus, changes in activity could be explained by both sintering of Cu particles and the phase change of the ZnO support. Inductively coupled plasma optical emission spectroscopy (ICP-OES) analysis of the solution after hydrogenation showed minimal catalyst leaching (Cu=2.2 ppm, Zn=5.1 ppm, Al≤1.3 ppm).

Figure 14:
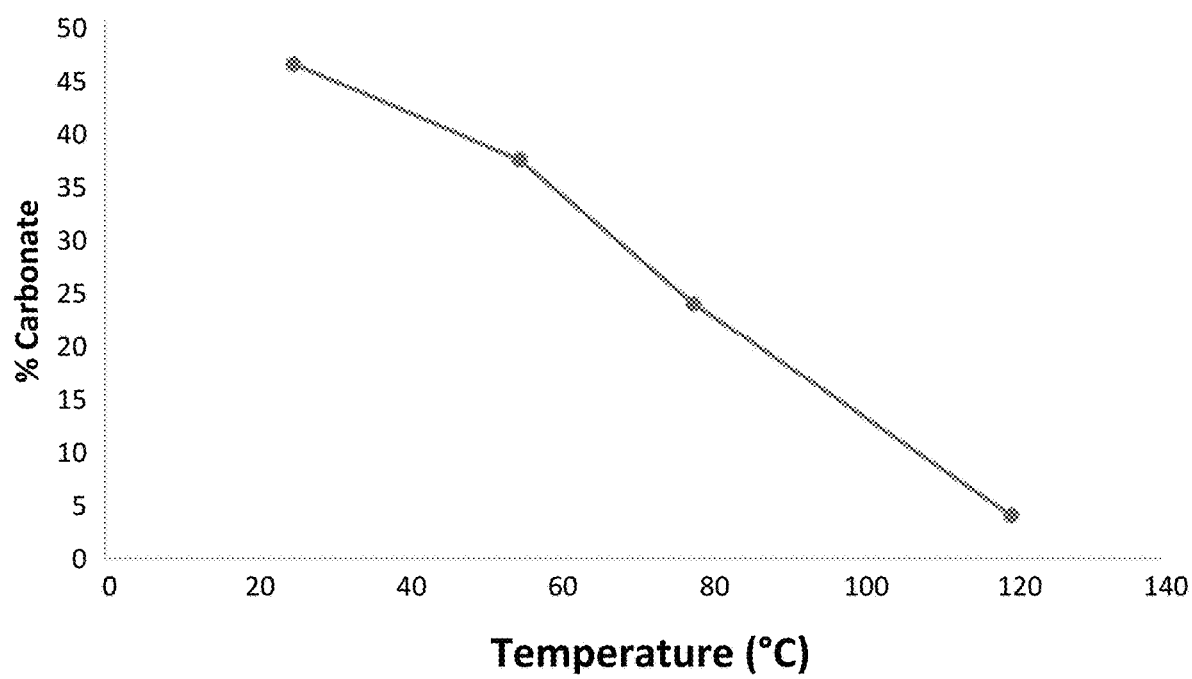
FIG. 14 is a graph percentage of ethyl carbonate formed with respect to total amine content vs. temperature.

MAS-NMR experiments were performed on an Agilent-Varian VNMRS NMR spectrometer equipped with an 11.7 T magnet, operating at 125.7747 MHz for the $^{13}C$ channel and 500.1822 MHz for $^1H$ channel, and using a 5 mm homebuilt MAS double-resonance HX probe with a custom Pd-coated coil for increased sample magnetic homogeneity. The rotor was heated to various set temperatures and both $^{13}C$ and $^1H$ spectra were collected before further temperature elevation. All rotors were Varian/Agilent-style cavern rotors (Revolution NMR LLC), modified for high pressure samples. 1:10 $NEt_3$:EtOH mixture (0.09 mmol: 0.9 mmol) and 4.7 mg of pre-activated $Cu/ZnO/Al_2O_3$ were transferred to a MAS NMR rotor in a $N_2$ glovebox. The rotor was charged with 2 MPa $CO_2$ at room temperature. Then the NMR of the initial reaction mixture was taken at 25° C., which showed the formation of triethylammonium ethylcarbonate ($EtOCO^-Et_3NH^+$) upon the reaction of free $CO_2$ with $NEt_3$ and ethanol. Subsequently the temperature was increased to 55, 78 and 120° C. The percentage of $EtOCO^-Et_3NH^+$ with respect to total amine content vs. temperature was plotted (FIG. 14).

Next, 4 MPa of hydrogen was introduced and the MAS rotor was heated at 170° C. for 8 h. The high-temperature operando $^{13}C$ magic angle spinning (MAS) NMR study of the catalyst in the presence of 1:10 $NEt_3$ and EtOH mixture at 2 MPa $CO_2$ at 120° C. showed ethylcarbonate (158.9 ppm) at a concentration 2.2 times that of the active sites of the catalyst. As shown in Table 1, 19% conversion to $CH_3OH$ was observed at 120° C., indicating that ethylcarbonate exists in a significant enough concentration to participate in the reaction at least up to this temperature.

Figure 15:
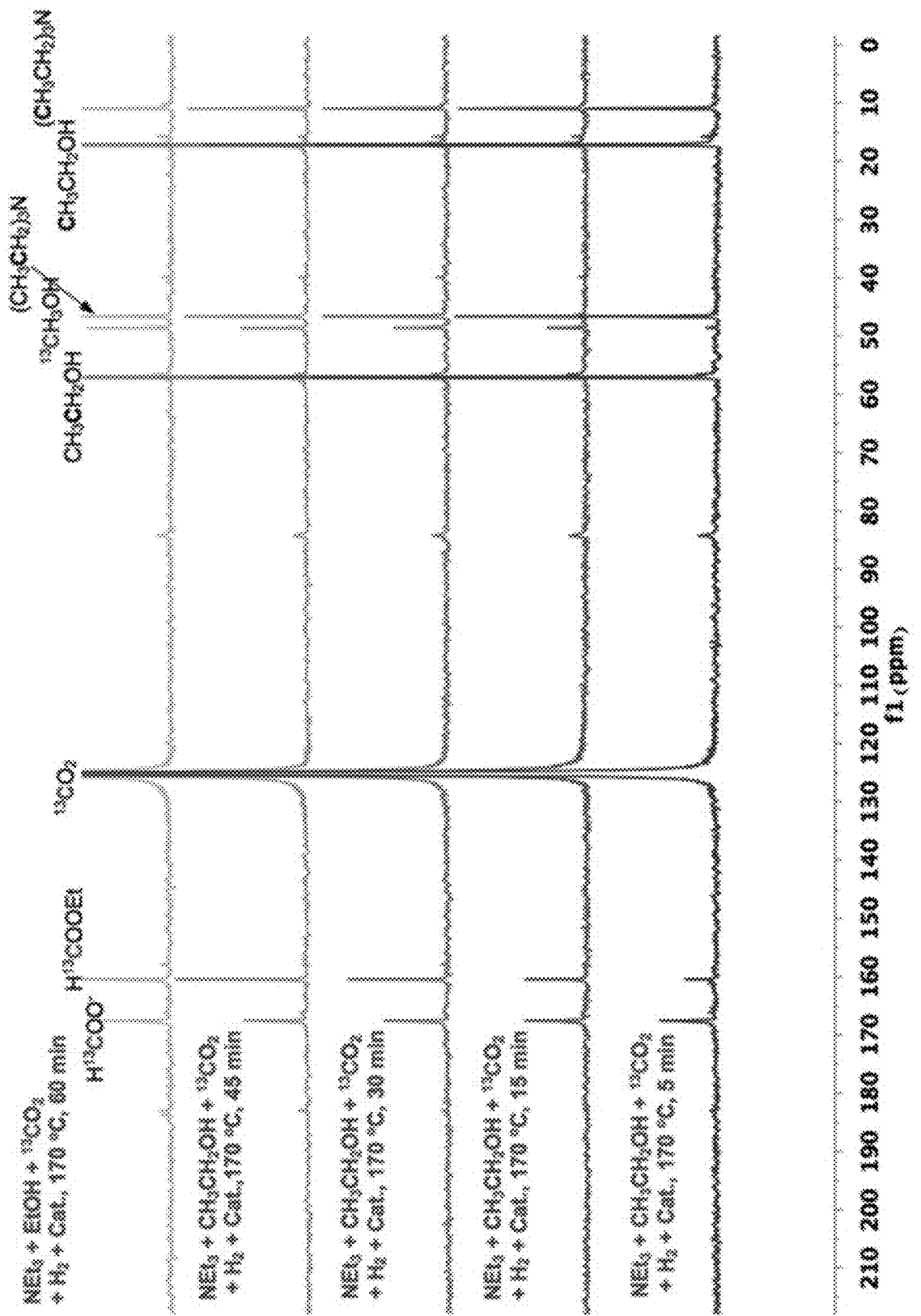
FIG. 15 shows in situ $^{13}$C MAS NMR of triethylamine: ethanol 1:10 reacted with $^{13}$CO$_2$ and H$_2$ in the presence of a Cu/ZnO/Al$_2$O$_3$ catalyst at 170° C. over one hour.

Operando $^{13}C$ MAS NMR at 170° C. in the presence of $H_2$ did not show a detectable amount of ethylcarbonate, though it clearly showed the formation of triethylammonium formate (168.5 ppm). The $CH_3OH$ signal at 48.7 ppm started to increase quickly in less than 5 minutes of heating at 170° C. (FIG. 15). Over time $CH_3OH$ decomposed into CO (182.2 ppm), confirming that the hydrogenation does not proceed via CO.

Figure 16:
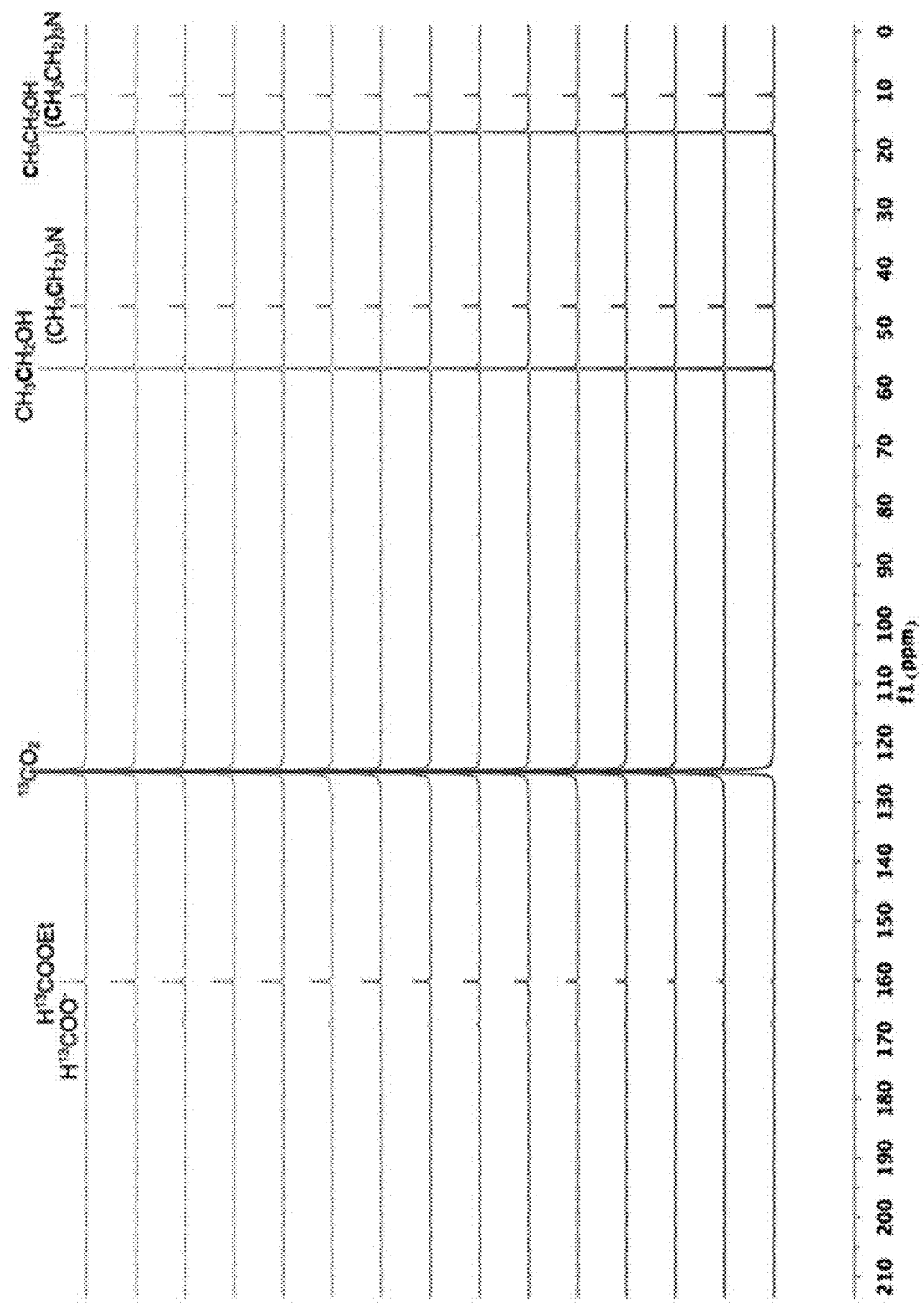
FIG. 16 shows in situ $^{13}$C MAS NMR of triethylamine: ethanol 1:10 reacted with $^{13}$CO$_2$ and H$_2$ in the presence of a Pd/ZnO catalyst at 170° C. over 15 h.

The $CO_2$ hydrogenation via the ammonium formate and alkyl ester intermediates in the presence of a Pd/ZnO catalyst under the same conditions was also studied. 1:10 $NEt_3$:EtOH mixture (0.09 mmol: 0.9 mmol) and 4 mg of pre-activated Pd/ZnO were transferred to a MAS NMR rotor in a $N_2$ glovebox. The rotor was charged with a 2 MPa $CO_2$ and 4 MPa of hydrogen at room temperature and the MAS rotor was heated at 170° C. for 15 h. There was no detectable amount of $CH_3OH$ observed by $^{13}C$ NMR at 170° C. (FIG. 16). However, slow accumulation of alkyl formate was observed over time.

Low-temperature condensed phase heterogeneous hydrogenation of $CO_2$ to $CH_3OH$ using $NEt_3$ and EtOH was demonstrated. The formation of side products such as CO and $CH_4$ was significantly reduced. Screening of various amines and alcohols revealed that alkyl carbonate, ammonium formate and alkyl ester were the key intermediates involved in the reaction which was confirmed by operando $^{13}C$ MAS NMR. The degree of alkyl carbonate and methanol formation was found to be limited by the solvent polarity as well as the basicity of the amine. Performing the present reaction in a flow system could significantly improve the overall productivity of the system, as poisoning of catalysts arising from the accumulation of products would be minimal.

Example 2

Cycloaddition of $CO_2$ to Epoxides

The formation of cyclic carbonates by addition of $CO_2$ to epoxides in a condensed phase comprising an amine was evaluated. A 100 mL Parr reactor was charged with a given amount of epoxide (propylene oxide, PO) and amine and sealed in a $N_2$-atmosphere glovebox. The reactor was then pressurized with 30 bar (3 MPa) $CO_2$ and heated to a set temperature for a given time. After the set time, the reactor was cooled to room temperature and then to 0° C., the excess pressure was released slowly. TMB (1,3,5-trimethoxybenzene, 100 mg) was added as an internal standard to the reaction mixture and a small aliquot of the sample was analyzed by $^1H$ and $^{13}C$ NMR experiments in $CDCl_3$. (Amidines were not used for this study because they tend to degrade at elevated temperatures under reductive conditions.) The reaction is shown below:

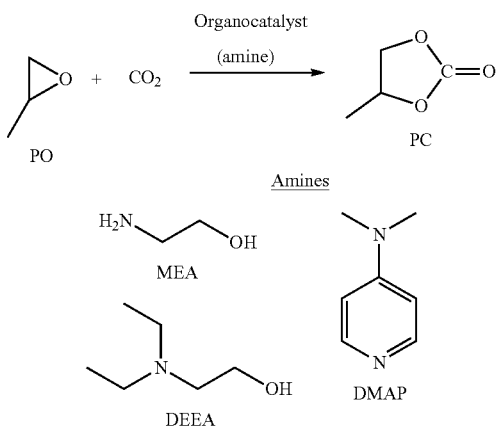

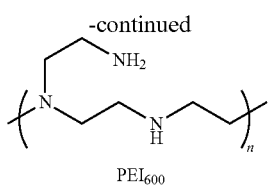

PEI$_{600}$

First, MEA, the most commonly used post-combustion CO$_2$ capture solvent, was studied for the formation of cyclic carbonate (entry 1, Table 4). MEA produced a very small amount of cyclic carbonate at 110° C. When a pre-combustion capture solvent, diethyl ethanol amine (DEEA), was used (entry 2, Table 4), only traces of cyclic carbonate was observed by $^1$H NMR experiment.

TABLE 4

| Entry | $^1$Amine | Temperature (° C.) | $^2$PC Conversion (%) |
|---|---|---|---|
| 1 | MEA (10 mol %) | 110 | 0.2 |
| 2 | DEEA (5 mol %) | 110 | traces |
| 3 | DMAP (10 mol %) | 110 | 58 |
| 4 | PEI$_{600}$ (300 mg) | 110 | 54 |
| 5 | PEI$_{600}$ (100 mg) | 110 | 11 |
| 6 | PEI$_{600}$ (100 mg) | 25 | 0 |
| 7 | PEI$_{600}$ (100 mg) | 140 | 97 |

$^1$Amines were in THF.
$^2$PC conversion % is relative to the epoxide amount.

4-dimethylaminopyridine (DMAP) was identified as one of the reactive bases that ring open epoxides via epoxide activation pathway (Scheme 2). Under our reaction conditions, a cyclic carbonate conversion of 58% was obtained with a good selectivity for P$_C$ (entry 3, Table 4). A high boiling polyamine (PEI$_{600}$) was also screened under the same reaction condition, and a cyclic carbonate conversion of 54% was achieved. Unlike DMAP, which was reported to first activate the epoxide, PEI$_{600}$ is expected to activate the CO$_2$, first via CO$_2$ activation pathway (Scheme 2) and subsequent nucleophilic attack of the carbanion on the epoxide, opens the ring and cyclizes to carbonate.

Upon the reaction of CO$_2$ with amines similar to PEI$_{600}$, a carbamic acid species, [—HN$^+$CO$_2^-$] is first formed, which then exists in equilibrium with carbamate, [—NH$^+$][—NCO$_2^-$]. Therefore, in addition to the CO$_2$ activation pathway described in Scheme 2, mechanism A, involving a carbamic acid intermediate, a competing reaction mechanism involving [—NH$^+$][—NCO$_2^-$] ion pair is also expected to occur. A DFT calculation of the reaction mechanism for the formation of cyclic carbonate from CO$_2$ and PO in the presence of DBU hexanol mixture suggested that after the initial activation of CO$_2$, the [DBUH$^+$][C$_6$H$_{13}$OCO$_2^-$] ion pair ring opens the epoxide (and not the [C$_6$H$_{13}$OCO$_2^-$] anion) and forms PC. Similarly, in the case of PEI$_{600}$, the [—NH$^-$][—NCO$_2^-$] carbamate ion pair ring opens the epoxide and liberates PC and regenerates [—NH$^-$][—NCO$_2^-$] carbamate under CO$_2$ atmosphere.

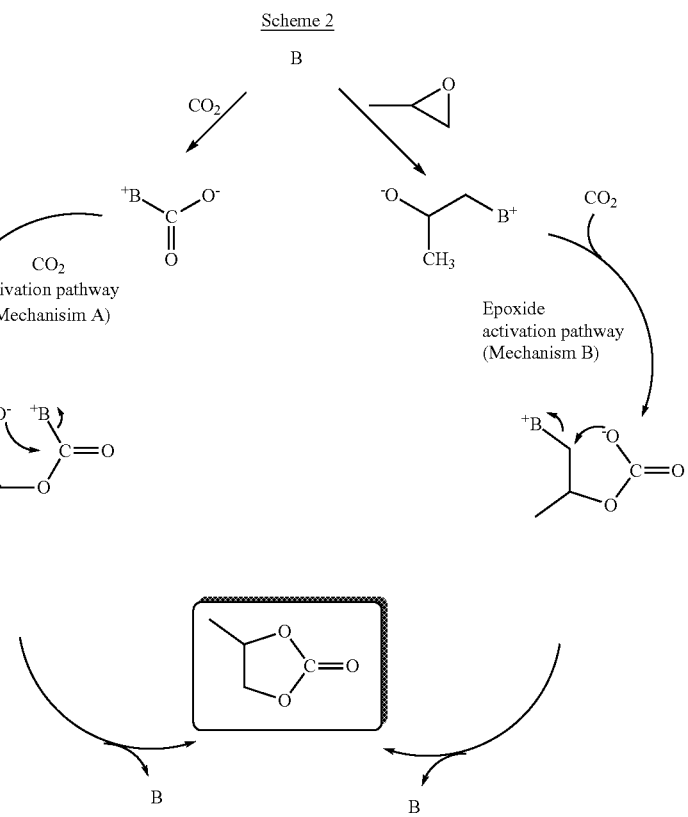

Scheme 2

PEI$_{600}$ was chosen for further optimization. Lowering the PEI$_{600}$ concentration significantly decreased the cyclic carbonate conversion to 11% (entry 5, Table 4). At room temperature, there was no detectable amount of PC observed, and the PO remained unreacted (entry 6, Table 4). Increasing the temperature to 140° C. resulted in increased cyclic carbonate yield of 97% with a selectivity of >99% (entry 7, Table 4).

Example 3

CO$_2$ Conversion to Methanol and Propylene Glycol

One- and two-step processes for converting CO$_2$ to methanol and propylene glycol (PG; also known as 1,2-propanediol, 1,2-PD) were evaluated. The reaction and catalyst are shown below. In the one-step process, propylene oxide (PO), a hydrogenation catalyst, and hydrogen were simultaneously added, and the propylene carbonate (PC) formed in step (a) immediately reacted with the catalyst and H$_2$ in step (b) to form methanol and 1,2-PD. Two-step processes included (i) reaction with PO (step (a)) followed by addition of the hydrogenation catalyst and hydrogen and subsequent reaction to form methanol and 1,2-PD (step (b)), and (ii) reaction with PO in the presence of the hydrogenation catalyst to form PC (step (a)), followed by addition of hydrogen and reaction to form methanol and 1,2-PD (step (b)).

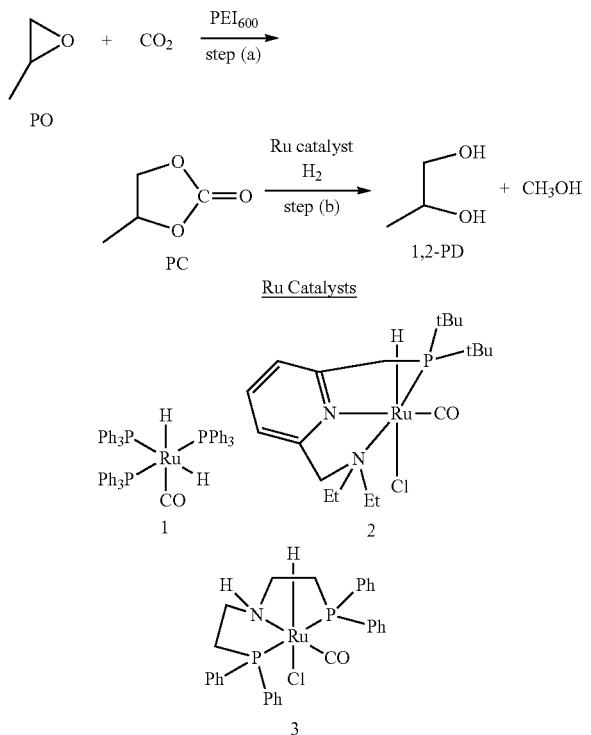

One-Pot One-Step Reaction:

A Parr reactor (100 mL) was charged with PO, PEI$_{600}$, metal catalyst and THF, and sealed in a N$_2$-atmosphere glovebox. The reactor was then pressurized with 20 bar CO$_2$ and 50 bar H$_2$ and heated to 140° C. for 24 h (total initial pressure=70 bar). After 24 h, the reactor was cooled to room temperature and then to −78° C., the excess pressure was released slowly. TMB (100 mg) was added as an internal standard to the reaction mixture and a small aliquot of the sample was analyzed by $^1$H and $^{13}$C NMR experiments in CDCl$_3$.

One-Pot Two-Step Reaction:

A Parr reactor (100 mL) was charged with PO, PEI$_{600}$ and THF, and sealed in a N$_2$-atmosphere glovebox. The reactor was pressurized with a 20 bar CO$_2$ and heated to 140° C. for 24 h. After 24 h, the reactor was cooled to room temperature and then to 0° C., the excess pressure was released slowly. The reactor was opened in the nitrogen atmosphere glovebox and the metal catalyst was added to the reaction mixture. Then the reactor was resealed and pressurized with a 60 bar H$_2$ and reheated to 140° C. for 16 h. After 16 h, the reactor was cooled to room temperature and then to −78° C., the excess pressure was released slowly. TMB (100 mg) was added as an internal standard to the reaction mixture and a small aliquot of the sample was analyzed by $^1$H and $^{13}$C NMR in CDCl$_3$.

One-Pot Two-Step Reaction—Sequential Addition of CO$_2$ and H$_2$:

A Parr reactor (100 mL) was charged with PO, PEI$_{600}$, metal catalyst and THF, and sealed in a N$_2$-atmosphere glovebox. The reactor was pressurized with a 20 bar CO$_2$ and heated to 140° C. for 16 h. After 16 h, the reactor was cooled to room temperature and then to 0° C., the excess pressure was released slowly. Then the reactor was pressurized with a 60 bar H$_2$ and reheated to 140° C. for 16 h. After 16 h, the reactor was cooled to room temperature and then to −78° C., the excess pressure was released slowly. TMB (100 mg) was added as an internal standard to the reaction mixture and a small aliquot of the sample was analyzed by $^1$H and $^{13}$C NMR experiments in CDCl$_3$.

Results are shown in Table 5.

TABLE 5

| Entry | PO (mmol) | Metal Catalyst | CO$_2$/H$_2$ (MPa) | PC (%) | PG (%) | CH$_3$OH (%) |
|---|---|---|---|---|---|---|
| 1$^a$ | 20 + PEI$_{600}$ | — | 2/5 | 96 | — | — |
| 2$^b$ | entry 7, Table 4 | 1 | 6 | 87 | 13 | — |
| 3$^b$ | entry 7, Table 4 | 2 | 6 | 4.8 | 95.2 | 69 |
| 4$^b$ | entry 7, Table 4 | 3 | 6 | 0 | >99 | 84 |
| 5 | 20 | 3 | 2/5 | 9 | 54 | 17 |
| 6$^c$ | 20 | 3 | 2/5 | 9 | 78.5 | 31 |
| 7 | 20 + PEI$_{600}$ | 3 | 2/5 | 12 | 84 | 32 |

Reaction conditions: THF = 5 g, t = 16 h, PO = 20 mmol, catalyst = 0.02 mmol, PEI$_{600}$ = 100 mg, T = 140° C.
$^a$24 h. Percent yields are relative to the epoxide.
$^b$The final reaction mixture from entry 7, Table 4 was hydrogenated in entries 2, 3, and 4 for 16 h.
$^c$36 h.

Figure 17:
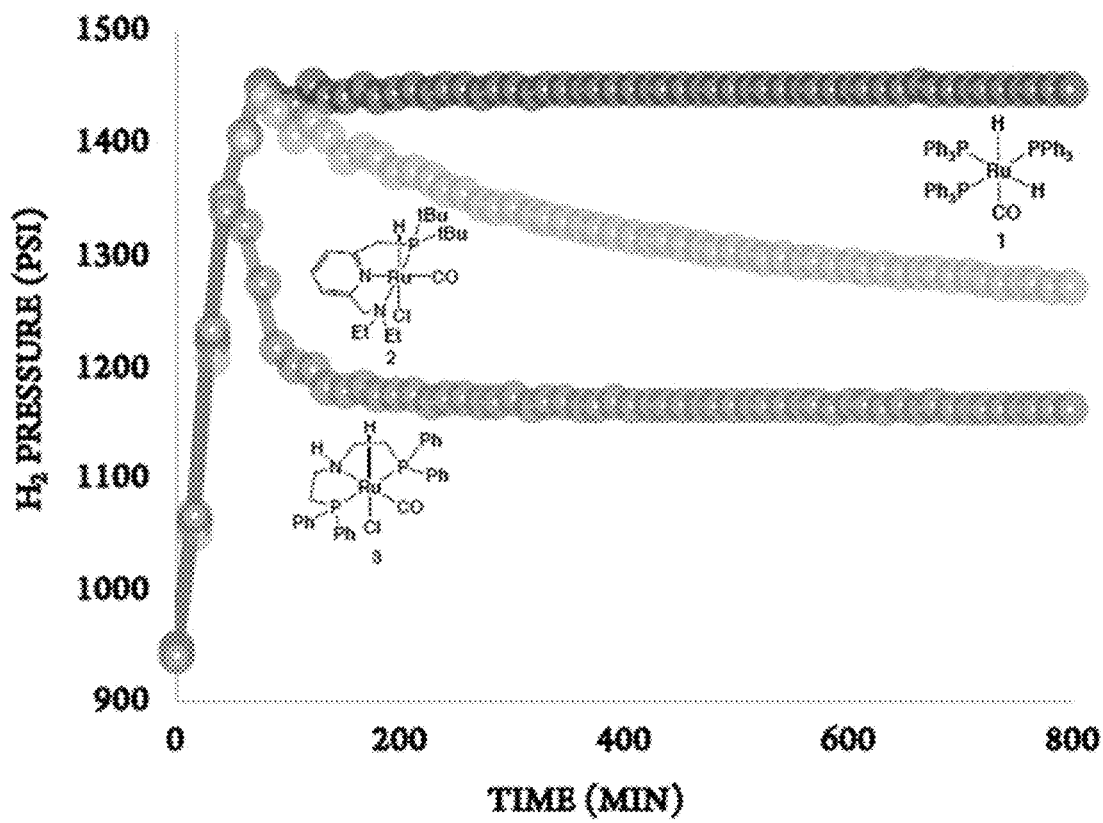
FIG. 17 is a graph showing the rate of hydrogenation of in situ-formed propylene carbonate in the presence of three ruthenium-based catalysts.

In the absence of a metal catalyst and only in the presence of PEI$_{600}$, there was no formation of methanol or glycol (Table 5, entry 1). Several Ru-based catalysts have been identified in the literature for hydrogenation of carbonyl moieties, from which a selected number of catalysts were screened for hydrogenation of in situ formed PC. Among the catalysts screened (Table 5, entries 2-4 and FIG. 17), the Ru-PNP pincer catalyst with the aliphatic backbone (catalyst 3) provided good yields for PG and methanol. The methanol yield was relatively lower than the PG yield because of the loss of methanol during depressurization of the reactor even at reduced temperature. Mass balance was confirmed by recreating the venting procedure and passing the gas through a cold trap to condense methanol. In addition, subjecting a 1:1 mixture of PG and methanol to the experimental reaction conditions (140° C., 16 h, 6 MPa H$_2$, THF solvent) and venting also resulted in the same glycol to methanol ratio. Gas chromatographic analysis of the vented gas showed only traces of CO from entry 4, Table 5.

Next, steps (a) and (b), which are the PC and PG (and methanol) formation steps, respectively, were combined. Even in the absence of $PEI_{600}$, methanol and glycol were formed, albeit at a lower reaction yield (entry 5, Table 5). Some of the PO remained unreacted (29%), and intermediates such as PC (9%) and formyl esters and amides (11%) were also observed by $^1$H NMR experiments. Longer reaction time resulted in improved PG and methanol yields (entry 6, Table 5), and 6.5% of the PO remained unreacted. Interestingly, the concentration of intermediates, PC (9%) and formyl esters and amides (11.5%), produced remained unchanged.

Figure 18:
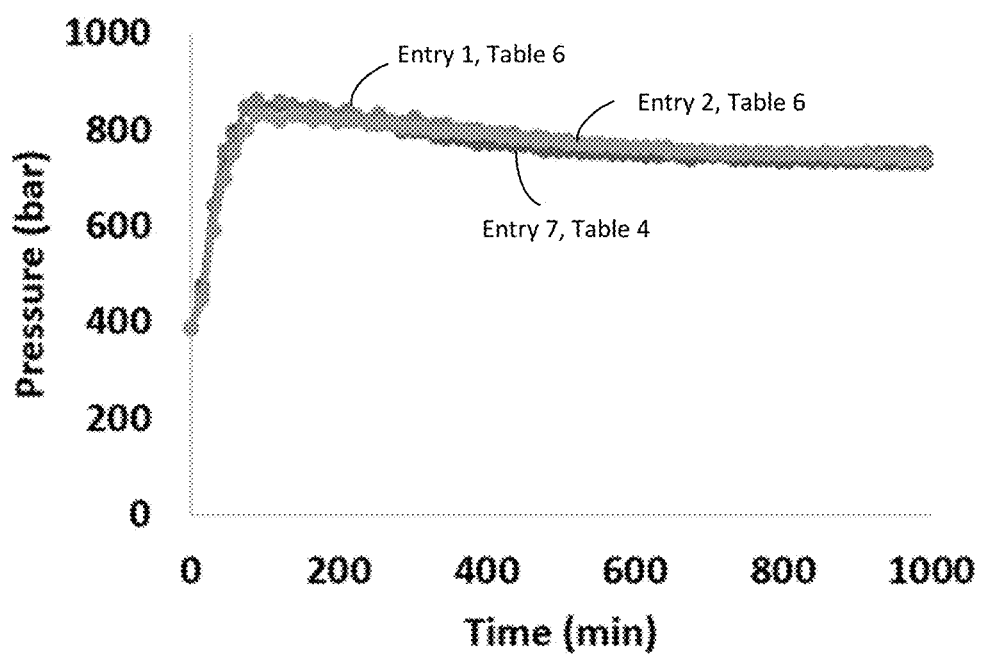
FIG. 18 is a graph showing the rate of cyclic carbonate formation from reaction of CO$_2$ and propylene oxide in the presence of two Ru-based catalysts and in the absence of a hydrogenation catalyst.
Figure 19:
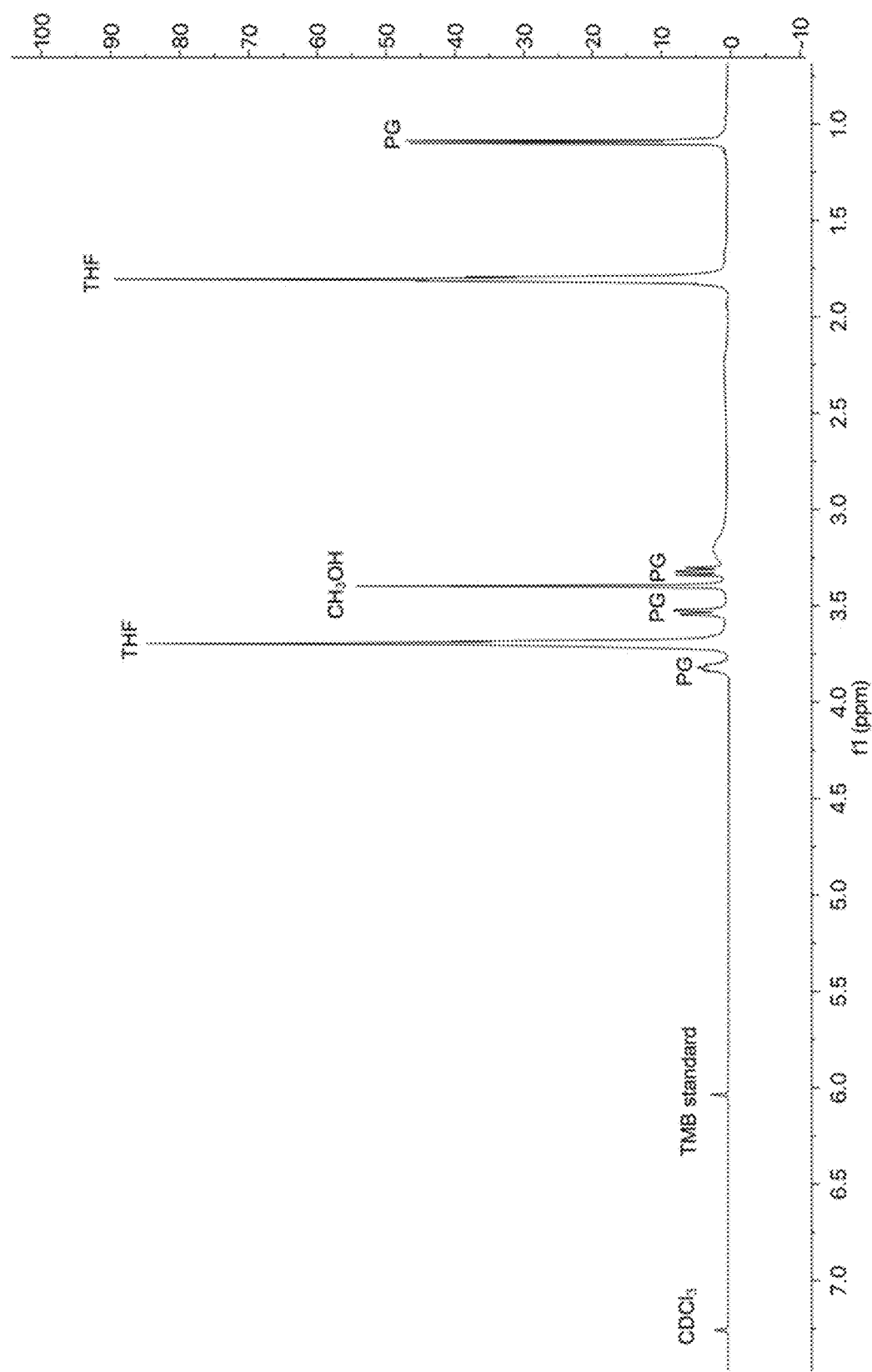
FIG. 19 is a $^1$H NMR spectrum of a reaction mixture after sequential addition of CO$_2$ and H$_2$ to a propylene oxide-PEI$_{600}$-tetrahydrofuran mixture in the presence of a Ru-based catalyst at 140° C.

Addition of $PEI_{600}$ increased PG and methanol yields (entry 5 vs entry 7, Table 5). There was no remaining unreacted PO. However, PC (12%) and formyl esters and amides (11%) were observed by $^1$H NMR. The addition of a metal catalyst for the second step required disassembly of the pressurized reactor, which may not be economical for practical application. Thus, the metal catalyst was added in step (a) along with PO, $PEI_{600}$, and $CO_2$. The $H_2$ was introduced subsequently in step (b). Results are shown in Table 6. Addition of catalysts 2 or 3 did not change the rate of formation of cyclic carbonate (FIG. 18) while catalyst 3 tolerated prolonged heating time during cyclic carbonate formation and remained active for the hydrogenation. The PG and methanol yields of >99% and 82%, respectively, were obtained based on $^1$H NMR (FIG. 19).

TABLE 6

| Entry | PO (mmol) | Metal Catalyst | PC (%) | PG (%) | $CH_3OH$ (%) |
|---|---|---|---|---|---|
| 1$^a$ | 20 + $PEI_{600}$ | 3 | 0 | >99 | 82 |
| 2$^b$ | 20 + $PEI_{600}$ | 2 | traces | >99 | 10 |

Reaction conditions: THF = 5 g, total time including cycloaddition (16 h) and hydrogenation (16 h) steps = 32 h, catalyst = 0.02 mmol, $PEI_{600}$ = 100 mg, $CO_2$:$H_2$ = 2 MPa/5 MPa (total pressure = 7 MPa), and T = 140° C.
Percent yields are relative to the epoxide.

Figure 20:
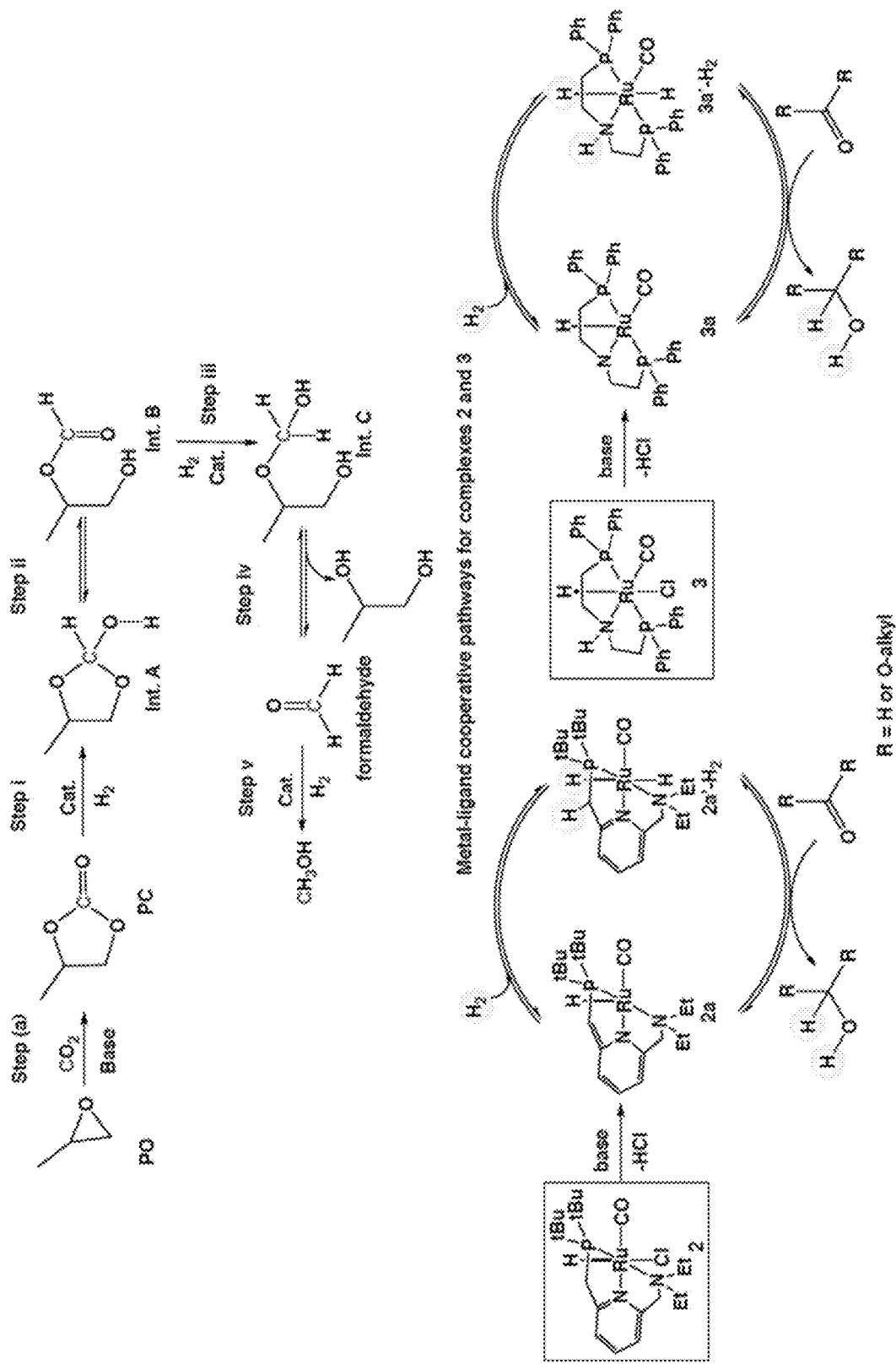
FIG. 20 shows one potential mechanism for formation of methanol and 1,2-propylene glycol from a reaction of CO$_2$, propylene oxide, and H$_2$ in the presence of a Ru-based catalyst.

Without wishing to be bound by a particular theory of operation, a plausible mechanism for the formation of methanol and PG is shown in FIG. 20. Upon initial activation of pre-catalysts 2 and 3 in the presence of a base, activated catalyst species 2a and 3a are formed. Heterolytic cleavage of $H_2$ on 2a and 3a yields dihydride complexes 2a'-$H_2$ and 3a'-$H_2$, respectively. The hydrogenation of $P_C$, Int. B, and formaldehyde is catalyzed by dihydride complexes 2a'-$H_2$ and 3a'-$H_2$ by a very well investigated metal-ligand cooperation via dearomatization (2a)/aromatization (2a'-$H_2$) or N—H site deprotonation (3a)/protonation (3a'-$H_2$) (Kuriyama et al., *Org. Process Res. Dev.* 2011, 16(1):166-171; Balaraman et al., *Nat. Chem.* 2011, 3(8):609-614; Han et al., *Angew. Chem. Int. Ed.* 2012, 51(52):13041-13045; Nielsen et al., *J Phys Chem C* 2018, 122(15):8209-8215). The hydrogenation of each intermediate species (carbonate, formate ester, and formaldehyde) was already reported in the literature by different groups in the presence of catalysts 2 and 3 (Kothandaraman et al., *J Am. Chem. Soc.* 2016, 138(3):778-781; Rezayee et al., *J Am. Chem. Soc.* 2015, 137(3):1028-1031; Han et al., *Angew. Chem. Int. Ed.* 2012, 51(52):13041-13045; Balaraman et al., *Nat. Chem.* 2011, 3(8):609-614). The reactivity for these intermediates was expected to decrease with decreasing electrophilicity in the following order: formaldehyde >formate ester (Int. B)>PC (Pritchard et al., *Chem. Soc. Rev.* 2015, 44(11):3808-3833). The protic hydrogen from the "$CH_2$" and "NH" cooperative sites of the ligands in dihydride complexes 2a'-$H_2$ and 3a'-$H_2$ interact with the carbonyl moieties of PC (Step i), Int. B (Step iii), and formaldehyde (Step v) and assist the nucleophilic attack by Ru—H and subsequent formation of Int. A, Int. C, and the final product, methanol.

Catalyst 3 was previously studied for $CO_2$ and CO hydrogenation to methanol via a formamide intermediate.

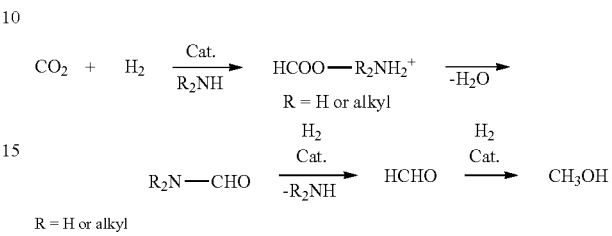

Figure 21:
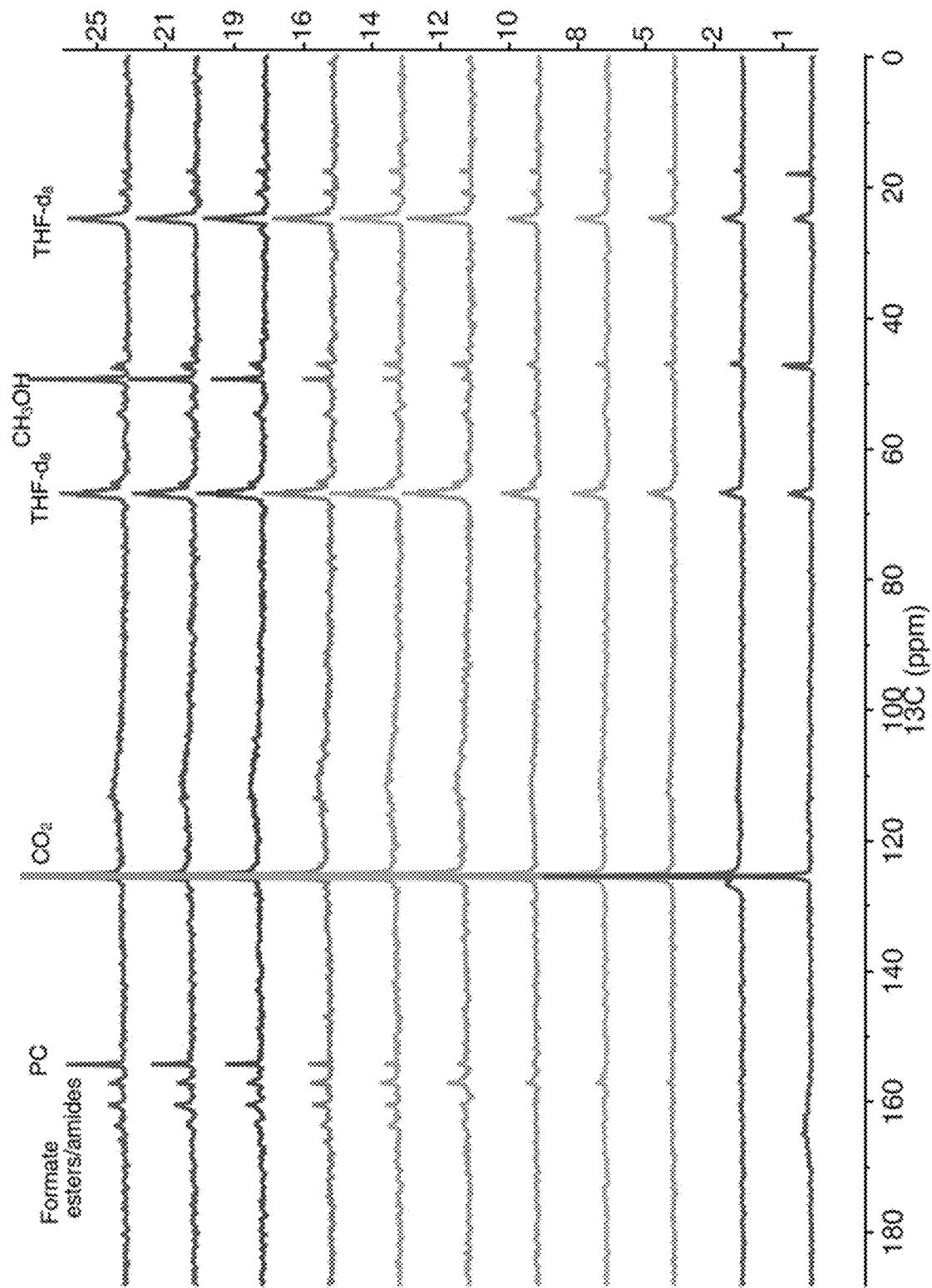
FIG. 21 shows in situ $^{13}$C MAS NMR of a one-step, one-pot reaction of propylene oxide with CO$_2$ and H$_2$ in the presence of a Ru-based catalyst.

To understand whether this competing reaction was occurring, operando MAS $^{13}$C NMR was performed at 140° C. under 6 MPa $CO_2$:$3H_2$ pressure (FIG. 21). Reaction conditions: 240 mg propylene oxide+60 mg $PEI_{600}$+2.4 mg catalyst 3 in THF-$d_8$ (1 mL) at 140° C. PC was the first intermediate that was formed, and the methanol concentration increased with increasing PC concentration. Formaldehyde was not observed, which suggests that it undergoes hydrogenation readily. There were multiple small signals that appeared between 158-168 ppm, which were attributed to formate esters and amides. Similar to what was previously observed for the experiments in Table 6 (entries 5 and 6), the concentration of these broadly assigned formate esters and amides did not change with reaction time. Informed simply by the $^{13}$C NMR, the direct hydrogenation of $CO_2$ via the formamide pathway could not be disregarded. However, the methanol yields never exceeded the glycol yields in any experiments. In addition, methanol was observed in experiments that did not have $PEI_{600}$ (entries 5 and 6, Table 5) and where the formamide could not be formed. Therefore, hydrogenation of $CO_2$ via cyclic carbonate (PC) is likely the major pathway. Unlike the formamide route (reaction (a), Scheme 4), no $H_2$ is wasted in the formation of water as a byproduct. Ultimately, with $H_2$ recycling, coproduction could result in a theoretical 100% atom efficiency.

Figure 22:
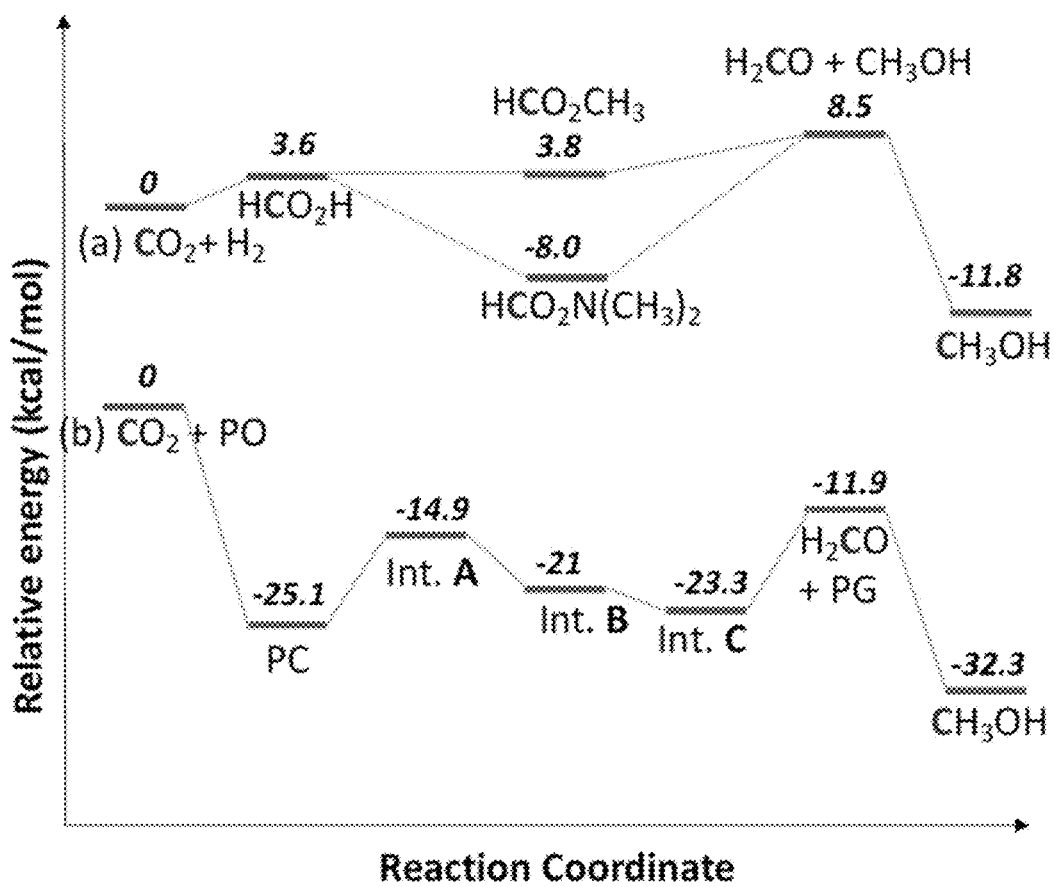
FIG. 22 is a diagram showing the energetics for coproduction of methanol and propylene glycol. Relative energies given are enthalpy of reactions. Routes (a) and (b) are conventional and the disclosed coproduction routes, respectively.

Thermodynamically, the coproduction of methanol and glycol (−32.3 kcal/mol) is more favorable than the individual reactions of −11.8 kcal/mol for direct $CO_2$ hydrogenation to methanol and −20.5 kcal/mol for hydrolysis of propylene oxide to PG. The energetics for the formation of methanol through $CO_2$ hydrogenation (a) is compared with the coproduction route (b) in FIG. 22. The presence of alcohols and amines is known to promote the formation of methanol in $CO_2$ hydrogenation as the reaction proceeds via formamide and ester intermediates (Kothandaraman et al., *J Am. Chem. Soc.* 2016, 138(3):778-781; Rezayee et al., *J Am. Chem. Soc.* 2015, 137(3):1028-1031; Everett et al., *Chem. Commun.* 2017, 53(68):9502-9504). The hydrogenation of ester and formamide are the rate limiting steps, which was identified by the inventors and others (Kothandaraman et al., *Catal Sci Technol* 2018, 8:5098-5103; Rayder et al., Chem 2020, 6:1-13). The N-formamide is 11.8 kcal/mol more stable than the ester intermediate and, accordingly, the ester is relatively more reactive than the formamide during hydrogenation.

A similar thermodynamic stability study of the intermediates involved in the coproduction process showed that propylene carbonate is the most stable intermediate and thus $P_C$ was the main intermediate identified by operando $^{13}C$ NMR (FIG. 21). The formaldehyde formation step is thermodynamically uphill from the starting materials ($CO_2$ and $H_2$) in the case of direct $CO_2$ hydrogenation; consequently, excesses of amines and alcohols are necessary to drive the reaction forward although they further complicate the separation process. On the other hand, in the case of the coproduction approach, a 1:1 mixture of glycol and methanol is produced without the need for excess alcohol or amine, therefore easing the separation process.

In conclusion, two commodity chemicals, methanol and propylene glycol, were produced directly from $CO_2$, $H_2$, and epoxide for the first time in one pot. $PEI_{600}$ was used for carbon capture and as an organocatalyst for the formation of a cyclic carbonate intermediate that was then hydrogenated in the same pot in the presence of Ru-PNP catalysts to produce methanol and propylene glycol. Operando $^{13}C$ NMR analysis showed the formation of mainly PC and small amounts of ester and amide intermediates under experimental reaction conditions. Unlike the low-temperature (<150° C.) direct $CO_2$ hydrogenation process in which an excess of alcohols and amines is used, the coproduction approach formed methanol along with glycol in good yields (>95% for PG and 84% for methanol) at 140° C. in the presence of a catalytic amount of amine and the Ru-PNP catalyst. In addition, the coproduction approach reduces the energy-intensive water separation process involved in the individual reactions, and eliminates the needed for added water and/or removal of any byproduct water since water is both generated and consumed in situ.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A process, comprising:
producing methanol and a glycol by combining an epoxide, a hydrogenation catalyst, hydrogen, and $CO_2$ with a condensed phase comprising an amine under conditions effective to provide a reaction between the epoxide, hydrogen, and $CO_2$ to form methanol and the glycol, wherein at least 10 mol % of the epoxide is consumed in the reaction.

2. The process of claim 1, wherein the condensed phase is a condensed phase solution further comprising the $CO_2$.

3. The process of claim 2, further comprising preparing the condensed phase solution by contacting a gas stream comprising $CO_2$ with an amine-containing solvent or solution prior to combining the epoxide, the hydrogenation catalyst, and the hydrogen with the condensed phase solution.

4. The process of claim 3, wherein contacting the gas stream with the amine-containing solvent or solution is performed:
(i) at a temperature T' within a range of from 20° C. to 60° C.; or
(ii) at an initial pressure P' within a range of from 0.1 MPa to 5 MPa; or
(iii) both (i) and (ii).

5. The process of claim 1, wherein the conditions effective to form methanol and the glycol comprise:

(i) a temperature $T_{MG}$ within a range of from 50° C. to 170° C.; or
(ii) an initial pressure $P_{MG}$ within a range of from 3 MPa to 10 MPa; or
(iii) a time $t_{MG}$ within a range of from 3 seconds to 36 hours; or
(iv) any combination of (i), (ii), and (iii).

6. The process of claim 1, further comprising:
(i) combining the epoxide, the $CO_2$, and the condensed phase under cycloaddition conditions effective to form a cyclic carbonate, thereby producing a cyclic carbonate-containing mixture, and
subsequently combining the cyclic carbonate-containing mixture with the hydrogenation catalyst and hydrogen under conditions effective to form methanol and the glycol; or
(ii) forming a mixture by combining the epoxide, the hydrogen catalyst, and the $CO_2$ with the condensed phase,
exposing the mixture to cycloaddition conditions effective to form a cyclic carbonate, thereby producing a cyclic carbonate-containing mixture, and
combining the cyclic carbonate-containing mixture with hydrogen under conditions effective to form methanol and the glycol.

7. The process of claim 6, wherein the cycloaddition conditions effective to form a cyclic carbonate comprise:
(i) a temperature $T_C$ within a range of from 25° C. to 180° C.; or
(ii) an initial pressure $P_C$ within a range of from 0.1 MPa to 2 MPa; or
(iii) a time $t_C$ within a range of from 3 seconds to 36 hours; or
(iv) any combination of (i), (ii), and (iii).

8. The process of claim 1, wherein:
the epoxide comprises

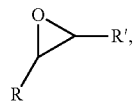

and
the glycol comprises R—CH(OH)—CH(R') (OH),
where R and R' independently are H or aliphatic, or R and R' together with the carbon atoms to which they are attached form a cycloaliphatic ring.

9. The process of claim 8, wherein R is methyl and R' is H.

10. The process of claim 1, further comprising:
(i) cooling the methanol and the glycol to a temperature within a range of from −100° C. to 30° C.; or
(ii) separating the methanol and the glycol from the condensed phase; or
(iii) separating the methanol and glycol from the condensed phase, and subsequently separating the methanol and the glycol; or
(iv) both (i) and (ii) or both (i) and (iii).

11. The process of claim 1, wherein:
(i) the amine comprises a 1° amine group, a 2° amine group, a 3° amine group, or any combination thereof; or
(ii) wherein the $CO_2$ is adsorbed, absorbed, covalently bound, or ionically bound to the amine; or
(iii) both (i) and (ii).

12. The process of claim 11, wherein the amine comprises a polyamine, a tertiary amine, a compound according to Formula I, or any combination thereof, the compound according to Formula I having a structure $R^1(R^2)N-L^1-NH-R^3$ where each of $R^1$ and $R^2$ independently is aliphatic or cycloaliphatic or $R^1$ and $R^2$ together with the nitrogen to which they are attached form a heterocyclyl ring, $L^1$ is aliphatic or cycloaliphatic or $L^1$ and $R^1$ together with the nitrogen to which they are attached form a heterocyclyl ring, and $R^3$ is aliphatic, cycloaliphatic, cycloalkylalkyl or alkoxyalkyl.

13. The process of claim 12, wherein the amine comprises polyethyleneimine (PEI), a compound according to Formula I, a tertiary amine, or any combination thereof.

14. The process of claim 1, wherein the condensed phase solution:
   (i) further comprises a nonaqueous solvent; or
   (ii) comprises from 0-10 wt % water; or
   (iii) both (i) and (ii).

15. The process of claim 1, wherein the hydrogenation catalyst comprises:
   (i) Ru, Pt, Pd, Rh, Ir, Ni, Co, Fe, Cu, Zn, a catalyst supported on alumina, carbon, silica, chromite, or a magnesium aluminum spinel, or any combination thereof; or
   (ii) a pincer ligand; or
   (iii) both (i) and (ii).

16. The process of claim 15, wherein the hydrogenation catalyst comprises

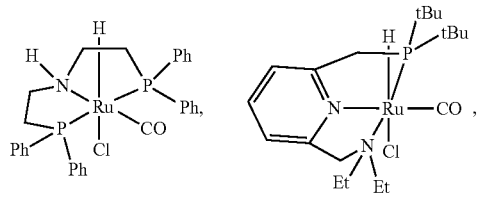

or a combination thereof.

17. The process of claim 1, wherein:
   (i) a molar ratio of $H_2$ to $CO_2$ is within a range of from 2:1 to 10:1; or
   (ii) the $CO_2$ is adsorbed, absorbed, covalently bound, or ionically bound to the amine, and the process is performed in an absence of $CO_2$ overpressure; or
   (iii) both (i) and (ii).

18. The process of claim 1, wherein:
   (i) the hydrogenation catalyst is disposed in a fixed bed or fluidized bed; or
   (ii) the process is a continuous process; or
   (iii) both (i) and (ii).

19. A process, comprising:
   producing methanol by combining a hydrogenation catalyst, hydrogen, and $CO_2$ with a condensed phase comprising an amine under conditions effective to provide a reaction between the hydrogen and $CO_2$ to form methanol and water, wherein at least 10 mol % of the $CO_2$ is consumed in the reaction;
   separating the methanol and water from the amine; and
   separating the methanol and water.

20. The process of claim 19, wherein the conditions effective to provide a reaction between the hydrogen and $CO_2$ to form methanol and water comprise:
   (i) a temperature $T_M$ within a range of from 50-180° C.; or
   (ii) an initial pressure $P_M$ within a range of from 1 MPa to 10 MPa; or
   (iii) a time $t_M$ within a range of from 3 seconds to 36 hours; or
   (iv) any combination of (i), (ii), and (iii).

* * * * *